(12) United States Patent
McCullough et al.

(10) Patent No.: US 9,448,148 B2
(45) Date of Patent: Sep. 20, 2016

(54) ROLLING WEIGHT DEFLECTOMETER

(71) Applicant: Quest Integrated, Inc., Kent, WA (US)

(72) Inventors: Robert W. McCullough, Kent, WA (US); Phillip Dewayne Bondurant, Covington, WA (US)

(73) Assignee: Quest Integrated, LLC, Kent, WA (US)

( * ) Notice: Subject to any disclaimer, the term of this patent is extended or adjusted under 35 U.S.C. 154(b) by 39 days.

(21) Appl. No.: 13/871,951

(22) Filed: Apr. 26, 2013

(65) Prior Publication Data

US 2013/0283924 A1    Oct. 31, 2013

Related U.S. Application Data

(60) Provisional application No. 61/792,997, filed on Mar. 15, 2013, provisional application No. 61/639,003, filed on Apr. 26, 2012.

(51) Int. Cl.
| | |
|---|---|
| *G01M 5/00* | (2006.01) |
| *G01N 3/00* | (2006.01) |
| *G01B 11/245* | (2006.01) |
| *E01C 23/01* | (2006.01) |

(52) U.S. Cl.
CPC ............... *G01N 3/00* (2013.01); *E01C 23/01* (2013.01); *G01B 11/245* (2013.01); *G01M 5/0058* (2013.01)

(58) Field of Classification Search
CPC ...... G01N 3/00; E01C 23/00; G01M 5/0058; G01B 11/245; G01C 7/04
USPC .......................................... 73/786, 146, 104
See application file for complete search history.

(56) References Cited

U.S. PATENT DOCUMENTS

| 4,958,306 | A | 9/1990 | Powell |
| 5,510,889 | A | 4/1996 | Herr |
| 5,753,808 | A | 5/1998 | Johnson |
| 6,040,853 | A * | 3/2000 | Delagnes et al. ............. 348/128 |
| 6,499,339 | B1 | 12/2002 | Hedström |
| 7,866,917 | B2 | 1/2011 | Malit |
| 2006/0274930 | A1 * | 12/2006 | Laurent et al. ............... 382/141 |
| 2012/0010828 | A1 * | 1/2012 | Ullidtz ........................... 702/42 |

OTHER PUBLICATIONS

International Search Report and Written Opinion mailed Aug. 19, 2013, issued in corresponding International Application No. PCT/US2013/038525, filed Apr. 26, 2013, 10 pages.

* cited by examiner

*Primary Examiner* — Harshad R Patel
*Assistant Examiner* — Brandi N Hopkins
(74) *Attorney, Agent, or Firm* — Chrsitensen O'Connor Johnson Kindness PLLC

(57) ABSTRACT

A device for measuring the deflection of pavement under an applied load includes a longitudinally extending member mounted on a mobile carriage. A load wheel is mounted near the first end of the longitudinally extending member below a load platform. A first distance sensor is mounted near the load wheel to measure the depth of a deflection basin created by the wheel at a target location disposed on the pavement. A second distance sensor mounted at a predetermined distance from the first sensor to measure distance to the target location when the second distance sensor is positioned proximate to the target location. The device further includes a target designator for designating the target location and a target detector for detecting a position of the target location.

13 Claims, 16 Drawing Sheets

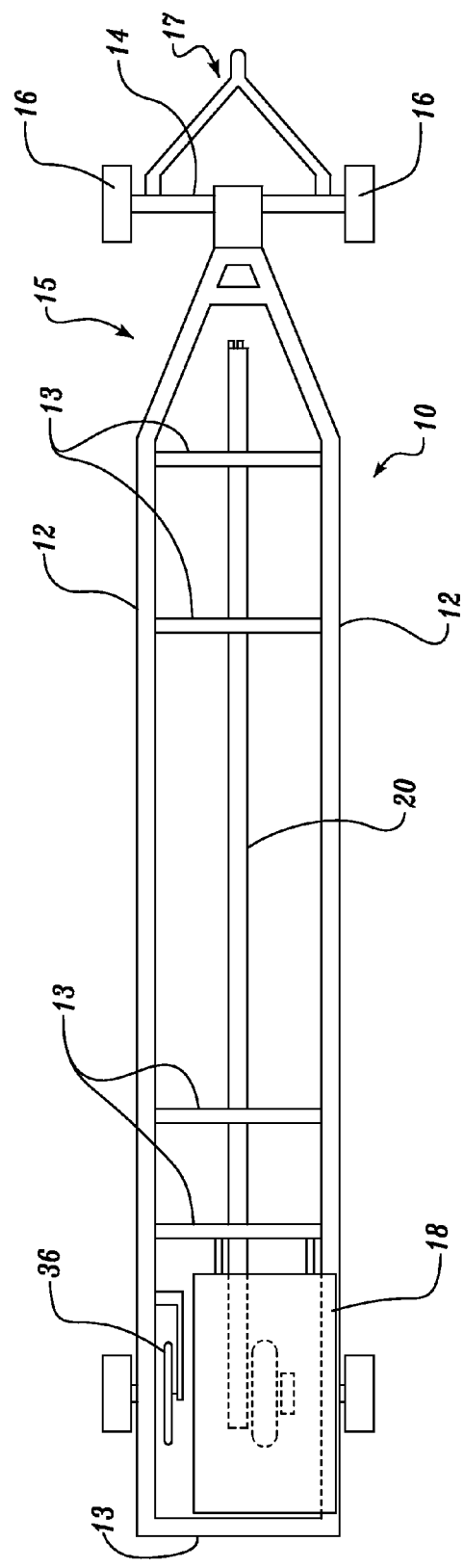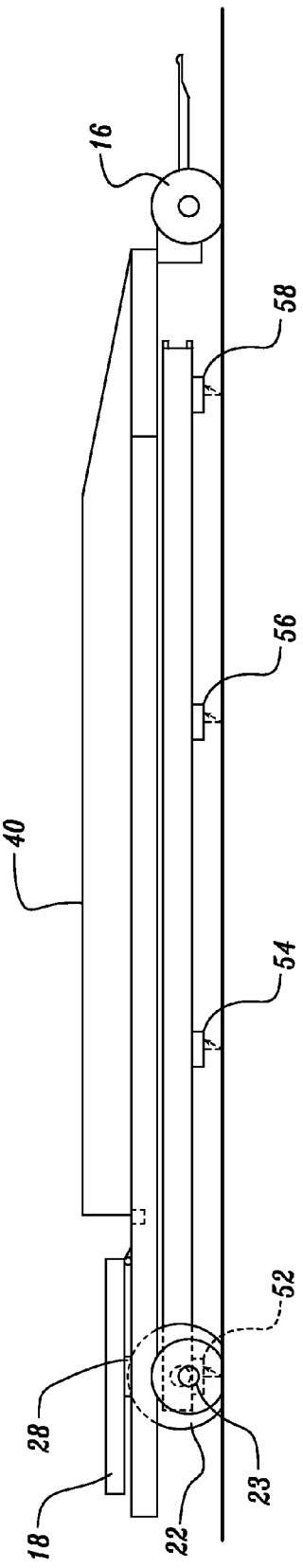
Fig.1.
Fig.2.

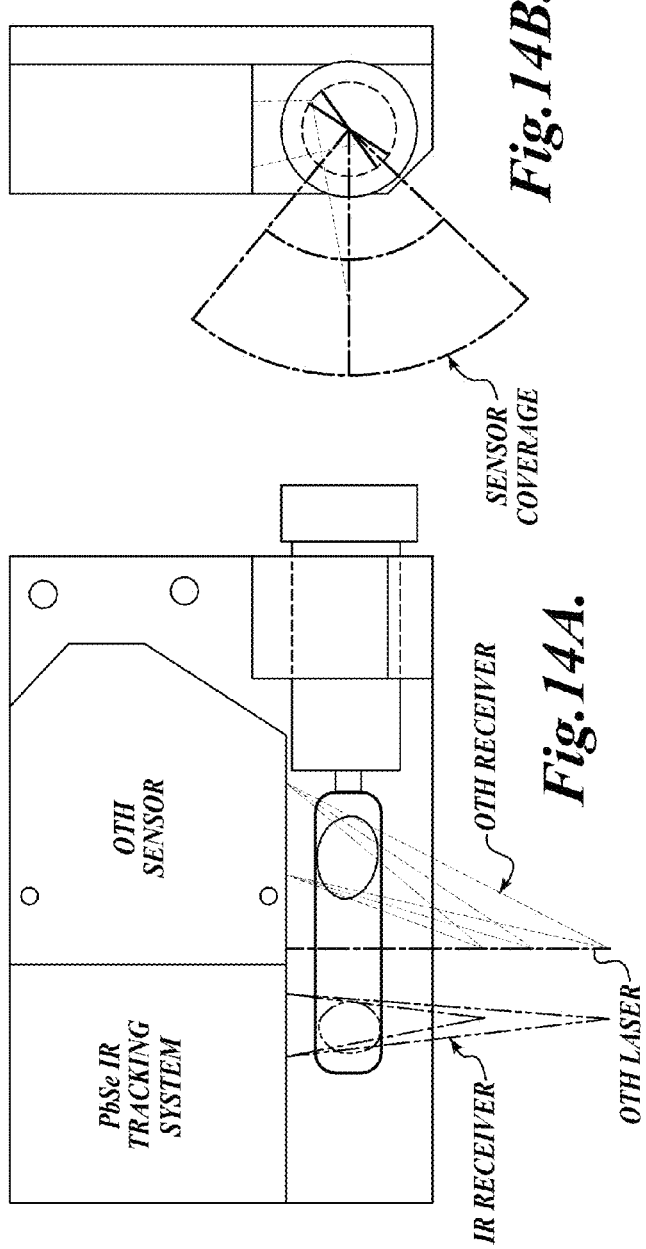
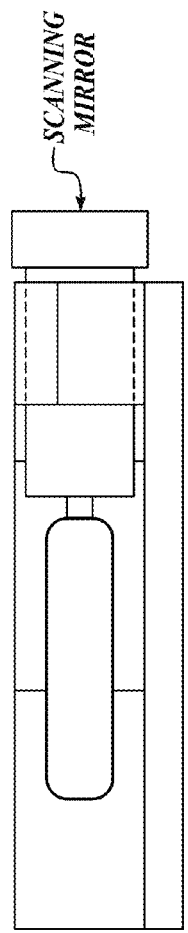
Fig.14B.
Fig.14A.
Fig.14C.

ROLLING WEIGHT DEFLECTOMETER

CROSS-REFERENCES TO RELATED APPLICATIONS

This application claims the benefit of U.S. Provisional Application No. 61/639,003, filed Apr. 26, 2012, and U.S. Provisional Application No. 61/792,997, filed Mar. 15, 2013, the disclosures of which are expressly incorporated by reference.

FIELD OF THE INVENTION

The invention relates to devices and methods for measuring the strength of pavement, especially concrete or asphalt pavement, by measuring its deflection under a known load. More particularly, the invention provides a rolling weight deflectometer, and measurement system for such a deflectometer, that compensates for inaccuracies in deflection measurements introduced by variations in the pavement measurement locations, thereby allowing more accurate measurement of pavement deflection under load.

BACKGROUND

In order to determine pavement condition for airport runways or highways, the load bearing capability of the pavement is periodically tested. Load bearing capability may deteriorate, over time, due to a number of factors, including changes in the elastic moduli of subpavement layers of earth. Thus, when subpavement earth layers subside or swell, their moduli are altered and affect the stability and load bearing capability of an overlying pavement. In order to measure the load bearing capability of the pavement, it is desirable to utilize technologies that are nondestructive so that the integrity of the pavement layer is maintained. Further, the measurements should desirably be made rapidly, through an automated system, to minimize time and reduce costs.

A rolling weight deflectometer may be used to continuously measure the deflection of a pavement. A device of this type is disclosed in U.S. Pat. No. 4,571,695 ("the '695 patent"). In essence, a load is placed on a wheel that rolls across the pavement and the depth of a deflection basin created by the loaded wheel is measured using precision laser sensors mounted on a horizontal member that tracks with the wheel. Such deflection measurements provide insight into the load bearing capability of the pavement. However, pavement deflections are usually very small, typically 0.010 to 0.040 inch for a 20,000 pound applied load. Therefore, not only are extremely sensitive sensors required to measure the deflection, but the sensors should have a stable reference plane. The deflectometer of the '695 patent fails to meet both of these requirements, as will be explained below.

FIG. 3 is a schematic representation of a rolling weight deflectometer, showing a member 20, a load wheel 22, and the pavement sensors 52, 54, 56, and 58. The upper schematic of FIG. 3 shows the horizontal bearing member at a first position on the pavement at time $t_1$, while the lower schematic shows the member at a second position at time $t_2$. The direction of travel of the member is indicated by an arrow and the amount of travel is metered by a "fifth wheel" (not shown). The reading or sampling control system of the apparatus is dependent upon the amount of rotation of the fifth wheel or odometer which sends electrical pulses to a computer to trigger the taking of measurements by the sensors. Thus, the pavement sensors are activated to take measurements at a spacing equal to the sensor separation distance. Sensor 52 measures that part of the depression basin formed that extends vertically below the sensor at $P_1$. This is not the exact maximum point of deflection, which should be directly beneath the center of load wheel 22. However, since the sensor is mounted as close as possible to a side of the wheel (typically, about 5 to 9 inches from the center of the wheel), the error introduced is acceptable. Likewise, equidistantly spaced sensors 54, 56, and 58 measure distances to points $P_2$, $P_3$, and $P_4$, respectively. After the trailer has moved forward by one sensor separation distance, the sampling control system is again activated by the rotation of the odometer wheel. Load wheel 22 has now moved so that a line drawn vertically through the axis of the sensor 52 passes through the point $P_2$ (in a statistical sense), where sensor 54 was previously positioned. Likewise, sensors 54, 56, and 58 have moved horizontally in the same direction for the same distance, so that sensor 54 is directly above $P_3$, sensor 56 is directly above $P_4$, and sensor 58 is directly above a new point, $P_5$. Thus, it is clear that a reading will be taken at each $P_n$, by the deflection basin measuring sensor 52, and each of the other sensors 54, 56, and 58, in a statistical sense. This assumes that the odometer wheel is accurate and precise, and that the trailer is traveling in a straight line.

FIG. 4 is a schematic showing the determination of the height of a point $P_i$ on pavement P above or below a horizontal theoretical datum line L. As shown, distance sensors 54, 56, and 58 are equally spaced. Sensor 54 is a distance C from a point $P_c$ vertically beneath the sensor on the pavement. Likewise, sensors 56 and 58 are distances B and A, respectively, from points $P_b$ and $P_a$ on the pavement. As for the description of FIG. 3, when the beam 20 is moved in the direction of travel indicated by the arrow, the odometer wheel (not shown) rotates and a second reading is taken such that sensor 52 (not shown), equally spaced from and left of sensor 54 and located nearest the load wheel, is a distance C' directly above $P_c$. Likewise, sensor 54 is above point $P_b$, sensor 56 is above point $P_a$, and sensor 58 has moved a distance to be above a new point (not shown). Thus, sensor 52 detects deflection of the pavement at statistically the same location where the unloaded pavement was measured by sensor 54. By continuing the pavement traversal process, sensor 52 measures statistically the same pavement, under load conditions, as measured by sensors 54, 56 and 58 under no load conditions.

The geometry of undeflected pavement is determined using leading sensors 54, 56, and 58, which are, in this example, equally spaced apart. Referring to FIG. 4, the point of contact $P_b$ of a laser beam from central sensor 56 with the pavement is at a measured distance B. A line is projected from $P_a$, a point of contact of a laser beam from sensor 58 through $P_b$, to intersect a laser beam extending vertically from sensor 54 to the pavement at point $P_i$. The distance that $P_a$ is below the datum line L, is given by (A-B). Similarly, from geometry, this distance (A-B) between point $P_i$ and the datum line L is reproduced. However, this does not account for the distance between the datum line L and $P_c$. Thus, h is defined as the distance between $P_c$ and $P_i$ and is called a "virtual height." Since sensors 54 and 58 are at equal elevation above datum line L, the following equality holds:

$$A-(A-B)=C-h+(A-B) \qquad (I)$$

This equation simplifies to:

$$h=A-2B+C \qquad (II)$$

In order to determine pavement deflection, the geometry of a second measurement, subject to the load wheel, is determined using sensors 52, 54, and 56. In this instance, the distance between sensors 52 and 54 may not be equal to the distance between sensors 54 and 56 and 56 to 58. The use of unequal distances between sensors allows the construction of a more compact rolling weight deflectometer. The following derivation of pavement deflection δ is based on a rolling weight deflectometer where the distances between sensors 52 and 54, 54 and 56 are each different. But, the distance between sensors 54 and 56, and sensors 56 and 58 are equal. To calculate the virtual height h', the same analysis as above is applied. Measured distances B, C, and D extend from sensors 56, 54, and 52, respectively, to the pavement surface directly beneath the sensors. The beams from sensors 56, 54, and 52, contact the pavement P at points $P_b$, $P_c$, and $P_d$, respectively. A theoretical straight line is projected from $P_b$ through $P_c$ to intersect the vertical laser beam emitted from sensor 52 (the sensor axis of sensor 52) at point $P_n$. The distance from $P_b$ to the theoretical horizontal datum line L is (B−C). By the geometry of similar triangles, the distance between the datum line L and $P_n$ is (n/m)(B−C). We can equate the elevation of the sensors:

$$B-(B-C)=D-h'+((n/m)(B-C)) \quad \text{(III)}$$

or, simplifying $$h'=(n/m)B-(1+(n/m))C+D \quad \text{(IV)}$$

where (n/m) is always greater than or equal to 1, and depends upon the relative spacing between the sensors.

Pavement deflection δ is then determined as:

$$h-h'=\delta \quad \text{(V)}$$

Aside from the factors discussed above, errors may be introduced into the h and h' calculations by thermal deformation of member 20. A member 20 of thickness H, thermal coefficient of expansion γ, and subject to temperature differential ΔT across its thickness, will be bent into a radius of curvature R, where: #

$$R = \frac{H}{\gamma \Delta T}$$

The deflection, d, at the center of the member of length L, will be:

$$d = R - \sqrt{R^2 - \frac{L^2}{4}}$$

If R is very much larger than L, then this simplifies to:

$$d = \frac{L^2 \gamma \Delta T}{8H}$$

For a member that is a steel beam 30 feet long with $\gamma = 11 \times 10^{-6}$ per °C., and H=10 inches, the thermal deflection is 0.018 inches/°C.

Since the deflections are typically in the range 0.015 to 0.040 inch for 20,000 pound loads, the thermally induced effect is about 50% of the maximum expected deflection.

Vibrational bending has similar deleterious effects on accuracy of deflection measurements. Vibration can be viewed as a dynamic type of member bending where member displacement varies with time. The actual effects are complex to model, but it is expected that the distance sensors would not each be displaced by the same distance from their horizontal alignment with each other.

Despite the sophistication and ease of use of the rolling weight deflectometer, the apparatus has inherent flaws that lead to significant errors in pavement deflection measurements. Measurements are based on several assumptions, including that the horizontal member remains absolutely straight and steady at all times. However, the horizontal member may bend due to thermal effects, despite sunshading, and may vibrate as the member is transported. Member bending introduces significant errors since pavement deflection is usually quite small, member bending effects are often large relative to actual pavement deflection. Also, it is assumed that the deflectometer tracks in a sufficiently straight line so that successive pavement distance sensors "see" the same spots on the pavement in deflected and undeflected condition. In practice, this assumption may not hold.

In addition, the following factors contribute to additional errors in pavement deflection measurements:

1) As the vehicle travels around curves in the road, the vehicle follows the trajectory of the road, while the height sensors, which are connected by a straight reference beam, follow different paths.
2) Measured deflections are small in comparison to pavement surface topology variation so that the spatially averaged height measured at one location might vary significantly if the average height is measured at a slightly offset location. Accordingly, the 3 sequential measurements of a given pavement location must be as close to the same position as possible.
3) Even on straight roads, it is difficult for the vehicle operator to maintain a straight line trajectory. Although increased vehicle speeds can mitigate this problem to a certain extent, vehicle wander is still a problem.
4) Road crown and road slope can cause the vehicle to "crab," wherein the path of the rear wheels of the trailer are offset laterally, i.e., to the left or right from the path of the front wheels. As a result, the 4 sensors on the reference beam view parallel lines of pavement as the vehicle moves forward.
5) Variations in road topology cause the vehicle and, therefore, the reference beam to roll, sway, and pitch.

There exists a need for a rolling weight deflectometer that compensates for variation in the location of the measured spot from one laser sensor to the next in order to provide more accurate measurements of pavement deflection under load. Further, the deflectometer should have all of the advantages of present rolling weight deflectometers, namely, ease of use, mobility, high sampling rate, and continuous operation to reduce the time and cost of taking measurements, as well as operator exposure to traffic. The deflectometer should also have built-in compensation for out-of-perfect straight line tracking of the trailer.

SUMMARY

A first claimed embodiment of a device for measuring the deflection of pavement under an applied load includes a longitudinally extending member mounted on a mobile carriage. A load platform is mounted on the carriage in the vicinity of a first end of the longitudinally extending member, and a load wheel is rotatably below the load platform in load bearing communication with the platform. The device further includes a first distance sensor mounted on the longitudinally extending member near the load wheel to measure the depth of a deflection basin created by the wheel at a target location disposed on the pavement. A second distance sensor is mounted on the longitudinally extending member at a predetermined distance from the first sensor to measure distance to the target location when the second distance sensor is positioned proximate to the target location. A target designator designates the target location, and a target detector detects a position of the target location.

A first claimed embodiment of a device for measuring the deflection of pavement under an applied load includes a longitudinally extending member mounted on a mobile carriage. A load platform is mounted on the carriage in the vicinity of a first end of the longitudinally extending member, and a load wheel is mounted below the load platform in load bearing communication with said platform. A first distance sensor is mounted on the longitudinally extending member, near the load wheel to measure the depth of a deflection basin created by the wheel at a target location disposed on the pavement. A second distance sensor mounted on the longitudinally extending member at a predetermined distance from the first sensor to measure distance to the target location when the second distance sensor is positioned proximate to the target location. The device further includes a surface profiler that scans the pavement proximate to the first distance sensor to generate a first surface profile and designate a feature of the first surface profile as the target location.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a schematic top view of an embodiment of a rolling weight deflectometer;

FIG. 2 is a schematic side view of the deflectometer of FIG. 1;

FIGS. 14A-14C show a schematic drawing of a second embodiment of a marker detector for a pavement designation system that uses a thermal marker to designate measurement location;

DETAILED DESCRIPTION

Figure 3:
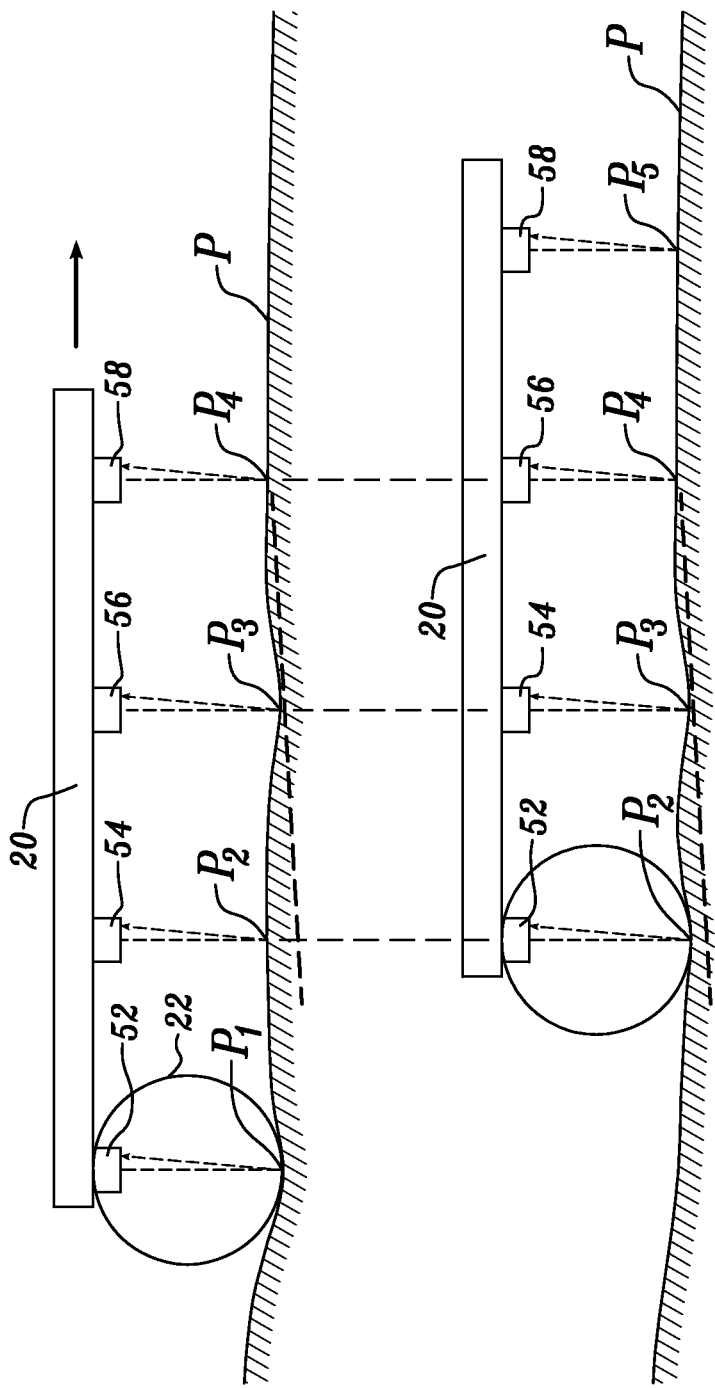
FIG. 3 is a schematic diagram illustrating principles of deflectometer operation.
Figure 4:
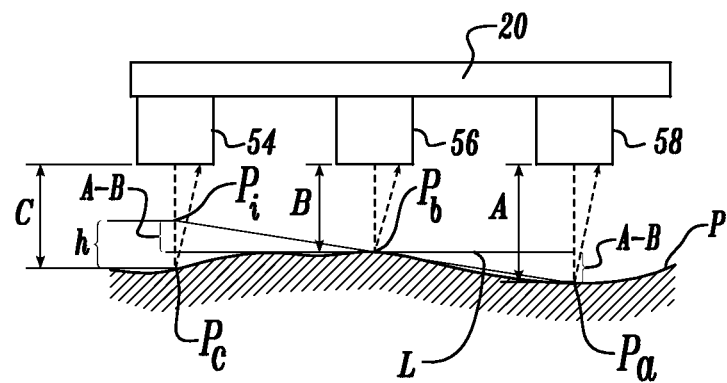
FIG. 4 is a schematic diagram illustrating principles of deflectometer operation.
Figure 5:
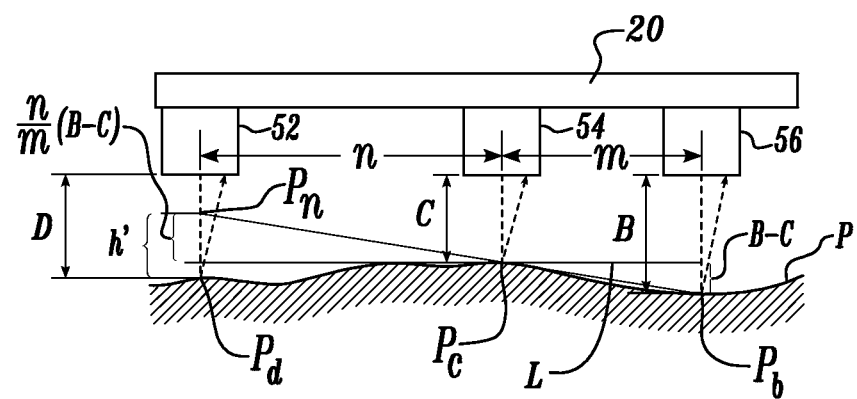
FIG. 5 is a schematic diagram illustrating principles of deflectometer operation.

Rolling weight deflectometers that measure the strength of pavement are presently known. For example, U.S. Pat. No. 5,753,808, issued to Johnson, ("Johnson") discloses a rolling weight deflectometers that takes utilizes a longitudinally extending, rigid, bearing member to which is mounted laser sensors for measuring the distance to a pavement, and consequently the degree of deflection of the pavement when it is subjected to a load transmitted by a load-bearing wheel. More specifically, the laser sensors measure multiple successive distances between a series of surface points on the pavement and the reference beam and uses these measurements to calculate the deflection of the pavement under the load bearing wheel.

In practice, implementation of the deflectometers such as the ones disclosed in Johnson, on actual roads results in inaccuracies in the deflection readings due in part to the following reasons.

The presently disclosed subject matter is directed to improved devices and methods for measuring the strength of pavement, especially concrete or asphalt pavement, by measuring surface deflection under a known load. The RWD of Johnson, which is incorporated by reference herein in its entirety, is described briefly below.

FIGS. 1 and 2 illustrate an exemplary rolling weight deflectometer. A mobile longitudinal support trailer 10 includes two parallel elongate support rails 12, interconnected at intervals with crossmembers 13 to form a ladder-like structure. At a forward end of the trailer, rails 12 converge to form a V-shaped structure 15 that is supported on an axle 14 supplied with wheels 16 at each end thereof. A trailer hitch 17 for towing the trailer is mechanically coupled to axle 14. At the opposite end of the trailer 10 is mounted a load platform 18. A load placed on load platform 18 is effectively transferred to axle 23, and thence to the load wheel 22. An odometer wheel 36 is rotatably mounted inside the frame of trailer 10 between support rails 12 and in the vicinity of load wheels 22 so that the wheel is in continuous contact with the pavement that the trailer traverses.

A rigid horizontal elongate member 20, usually metal of I-shaped or box-shaped cross-section, is mounted centrally in the trailer between and substantially parallel to support rails 12, in a suspended mount from cross ties 13. The member is of sufficient length to extend from the load axle 23 toward the forward end of the trailer so that pavement locations directly beneath a forward portion of the member are substantially unaffected by a deflection basin formed beneath load wheel 22. Four pavement sensors 52, 54, 56, and 58 are fixedly mounted to member 20, and are spaced apart at known intervals, such as the equal intervals shown. Pavement sensor 52 is positioned near axle 23 to measure the depth of a deflection basin formed when a line of contact of a load wheel 22, typically a standard aircraft wheel, passes over a section of pavement. Pavement sensors 54, 56 and 58 are positioned on a portion of member 20 sufficiently far from axle 23 so that their measurements are not affected by the deflection basin formed by the load wheel.

The following description gives details of the preferred embodiment of the rolling weight deflectometer of the invention, and illustrates its benefits. As explained above, the virtual heights h and h' of any point on a pavement may be calculated using equations (II) and (V). The difference, h'−h, gives the pavement deflection under load. However, when the horizontal sensor-carrying member is bent, so that the pavement sensors are not collinear when a distance measurement is made, then this introduces an error into the virtual height determinations, and consequently into the calculated pavement deflection.

Figure 6:
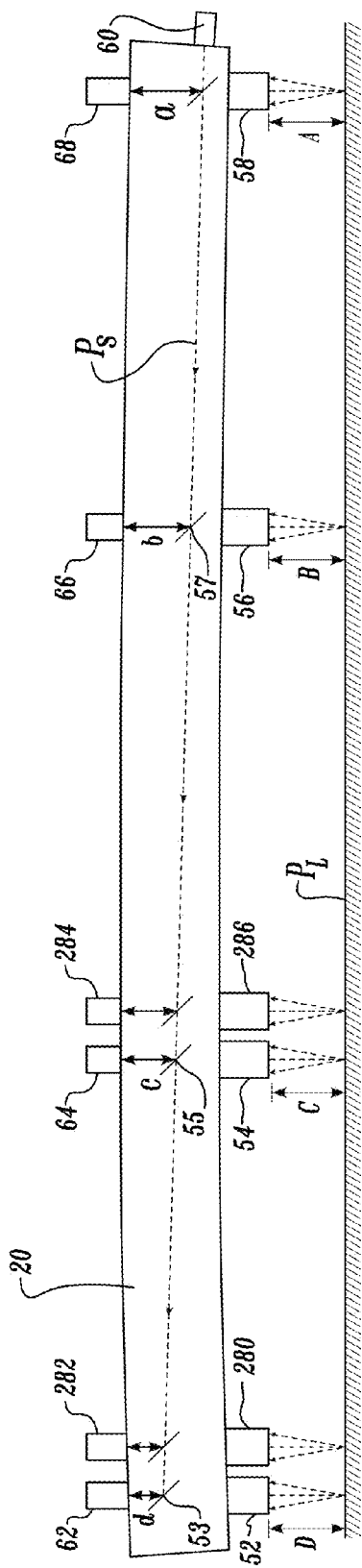
FIG. 6 is a schematic diagram of an embodiment of the invention showing the alignment laser beam emitter.
Figure 7:
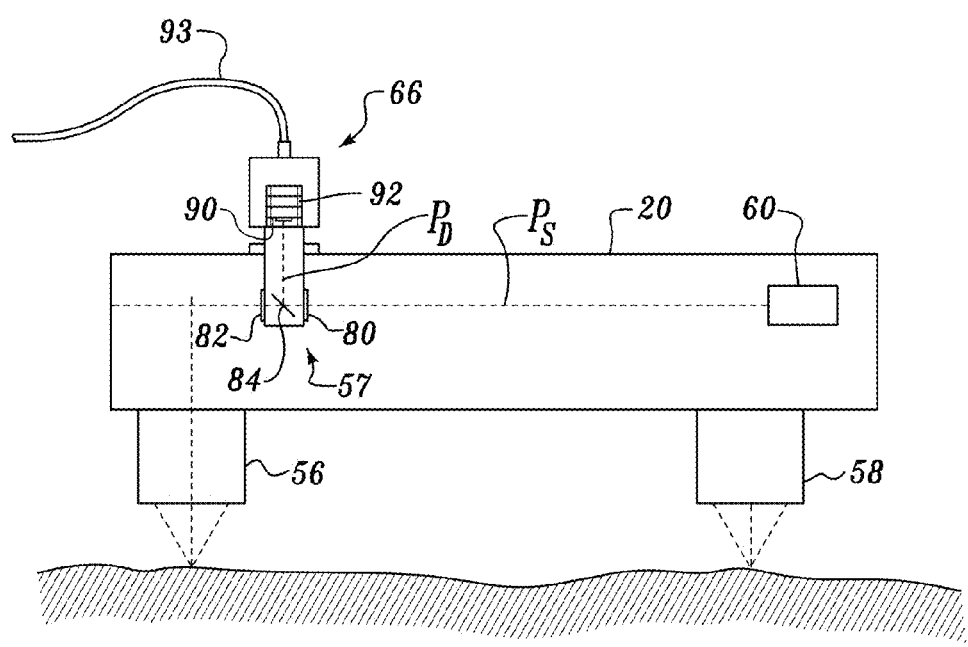
FIG. 7 is a schematic diagram illustrating pertinent details of an embodiment of the beam straightness sensors and beam deflectors of the invention for determining a bent member compensation factor.

To compensate for the error introduced into sensor distance measurements by bending of member 20, the invention provides an alignment laser emitter 60, mounted near an end of member 20 that directs a reference laser beam $P_s$ along the member, as shown in FIG. 6. Beam straightness sensors 62, 64, 66, and 68, each adapted to receive a laser beam, are mounted vertically above and aligned with each of the distance sensors 52, 54, 56, and 58, respectively. Laser beam splitters (not shown in FIG. 6), such as 45° cube beam splitters or pellicles, are mounted at points 53, 55, 57, and 59, to intercept and deflect a portion of the laser beam $P_s$ to each of the straightness sensors 52, 54, 56, and 58, respectively, as shown in FIG. 7. Preferably, about 15% of incident beam energy is deflected. The position of the centroid of intensity of the deflected portion of the reference laser beam is precisely measured using a lateral effect photodiode or CCD array. The deflected beam strikes a position sensitive photodetector on each of the straightness sensors, thereby providing a measurement of the displacement of each pavement distance sensor relative to the reference laser beam $P_s$. When the member 20 bends or vibrates, while the rolling weight deflectometer is in use, the spatially sensitive photodetector will move or be displaced relative to the laser beam $P_s$. This displacement causes the point of laser incidence on the photodetector of the straightness sensor to be displaced. This displacement provides a basis for compensating the measurements taken by an associated pavement sensor for movement of the horizontal member.

The member straightness sensors and laser beam deflectors useful in the invention are shown schematically in FIG. 7. A member straightness sensor 66 is mounted on longitudinal member 20. Associated with the member straightness sensor 66, is a pavement distance sensor 56, mounted to member 20 such that the distance from the laser to the middle of the pavement sensor 56 is equal to the distance from the laser to the beam splitter 84 plus the additional distance from the beam splitter to the surface of the position sensitive photodetector in the vicinity of the member straightness sensor. An alignment laser beam emitter 60 is mounted near a forward end of member 20, near pavement distance sensor 58. Alignment laser beam emitter 60 emits a reference laser beam $P_s$ substantially along the length of longitudinal member 20. Reference beam $P_s$ is incident upon a laser beam deflector 57 associated with member straightness sensor 66. The laser beam deflector has a window 80 aligned to receive the reference laser beam as an incident laser beam, a beam splitter behind the window angled to reflect a portion of the incident laser beam at an angle of 90° and transmit the remainder of the laser beam through an exit window 82. The deflected portion of the reference laser beam $P_d$ strikes a horizontally mounted position sensitive photodetector 90 or CCD array at a specific point. Digital signal processing electronics 92, associated with the position-sensitive photodetector 90, convert relative lateral movement between deflected beam $P_d$ and position sensitive photodetector 90 into a distance measurement. For example, when member 20 bends so that pavement distance sensor 56 is deflected downward, reference laser beam $P_s$ is incident upon a higher point on beam splitter 84, thereby shifting the point of incidence of deflected laser beam $P_d$ on the photodetector toward the left. This displacement toward the left is measured and converted by the digital signal processor 92 into an equivalent vertical displacement of member 20.

The error in distance measurement made by a pavement distance sensor that is introduced by bending of the member 20 is offset by adding the distance of a straightness sensor from the reference laser beam $P_s$ to the distance measured by the pavement distance sensor, associated with that straightness sensor. Thus, the effective distances to be used for each of the sensors shown in FIG. 6, and by the deflection algorithm, equation (V), are as follows:

$$\text{Distance sensor } 52 = D + d$$

$$\text{Distance sensor } 54 = C + c$$

$$\text{Distance sensor } 56 = B + b$$

$$\text{Distance sensor } 58 = A + a$$

where capital letters represent the pavement distance sensor measurements and lower case letters are the straightness sensor measurements.

Clearly, reference beam $P_s$ need not be perfectly horizontal nor remain horizontal. Indeed, $P_s$ may be inclined at an angle. Since $P_s$ is a beam of light, it may be assumed that it is perfectly straight so that it serves as an invariant straight reference line. When the alignment laser beam emitter is located at or near distance sensor 58, then only sensors 52, 54, and 56 require beam straightness sensors since the distance "a" may be set at zero. The straightness sensors are preferably mounted such that the distance from laser 60 to beam splitter 84 and thence to position-sensitive photodetector 90 is equal to the distance between corresponding pavement sensors. Thus, straightness sensors will be mounted ahead of the middle of each of the pavement sensors by a distance equal to the distance from the beam splitter to the position-sensitive photodetector.

According to the invention, distance sensors 52, 54, 56, and 58 take measurements at a point on the pavement and virtual heights h and h' are calculated using the following equations:

$$h=(A+a)-2(B+b)-(C+c) \quad (VI)$$

$$h'=(B+b)-2(C+c)+(D+d) \quad (VII)$$

The difference between these virtual heights (h-h') for four equally spaced pavement distance sensors is the deflection, according to the invention.

The odometer wheel rotation activates the sampling circuit for the pavement distance sensors. Distance measurements are taken at about 1 millisecond intervals when the deflectometer travels at about 4 miles per hour. At higher speeds of travel, shorter sampling intervals may be used. The laser beams from the distance sensors are about two inches (50 mm) wide, perpendicular to direction of carriage travel, and one inch (25 mm) in the direction of carriage travel. Typically, about 100 measurements are taken at each sampling point by each of the distance sensors, although more or less may be taken. The distance between sampling measurements may vary, depending upon the pavement being tested and speed of trailer traversal of the pavement. Typically, a distance of 0.70 inch (18 mm) traverses the pavement at a rate of about 4 mph (6 kph) at a sampling rate of ten measurements at 1 KHz.

In general, in the method of using the odometer, in accordance with the invention, the odometer wheel is first set to a starting position. When the odometer wheel has traversed a predetermined distance, set by the operator and depending upon the speed of trailer traversal of the pavement (typically about one foot (25 cm) or an integer multiple thereof), measurements are taken at each of the distance sensors. Simultaneously, the straightness sensors compensate for each of the readings taken at the pavement distance sensors, thereby allowing more accurate calculation of pavement deflection. Preferably, all readings are stored in electronic memory of the digital signal processor for subsequent retrieval and manipulation.

According to the invention, the preferred height sensors are those that operate on a principle of dual symmetric triangulation. These sensors utilize a laser beam that is collimated to an elliptical shape, with the longest axis, preferably about two inches (50 mm), perpendicular to the direction of travel of the deflectometer, and the shorter axis, preferably about one inch (25 mm) parallel to the direction of travel. Further, the device utilizes a spatially sensitive detector known as a "lateral effect photodiode." Preferably, the device has a 30° angle between the direction of incident laser light on the measured surface and the axis of the viewing lens. Both detectors and the optical systems are arranged in mirror symmetry about the incident laser beam. The dual symmetric triangulation approach may be better understood with reference to FIG. 8 which shows a schematic of an embodiment of a height sensor constructed to use these optical principles. As illustrated schematically, the pavement sensor includes a housing 100 with a window 95 on one side through which laser beams may pass. A laser beam 101 is emitted from laser emitter 94 through window 95 to the pavement surface 98. Reflected returning laser beams 102, 103, enter the window 95 and are focused through focusing lenses 114 and 112, respectively, each of the lenses being equidistantly spaced on either side of emitted laser beam 101 and having optical axes preferably at about 30° to the emitted beam, although other angles are also useful, depending on deflectometer geometry. The focused beams are then incident upon spatially sensitive photodetectors 116 and 118, located behind lenses 114 and 112, respectively. The detectors are oriented at an angle with respect to the optical axes of the lenses so that the imaged laser spot is in focus throughout the measuring range. This angle satisfies the Schiempflug condition. Preferably, the housing also contains digital signal processing electronics 97 in electrical communication with each of the photodetectors to interpret the movement of the point of incidence of a laser beam on the spatially sensitive photodetector surfaces.

Figure 8:
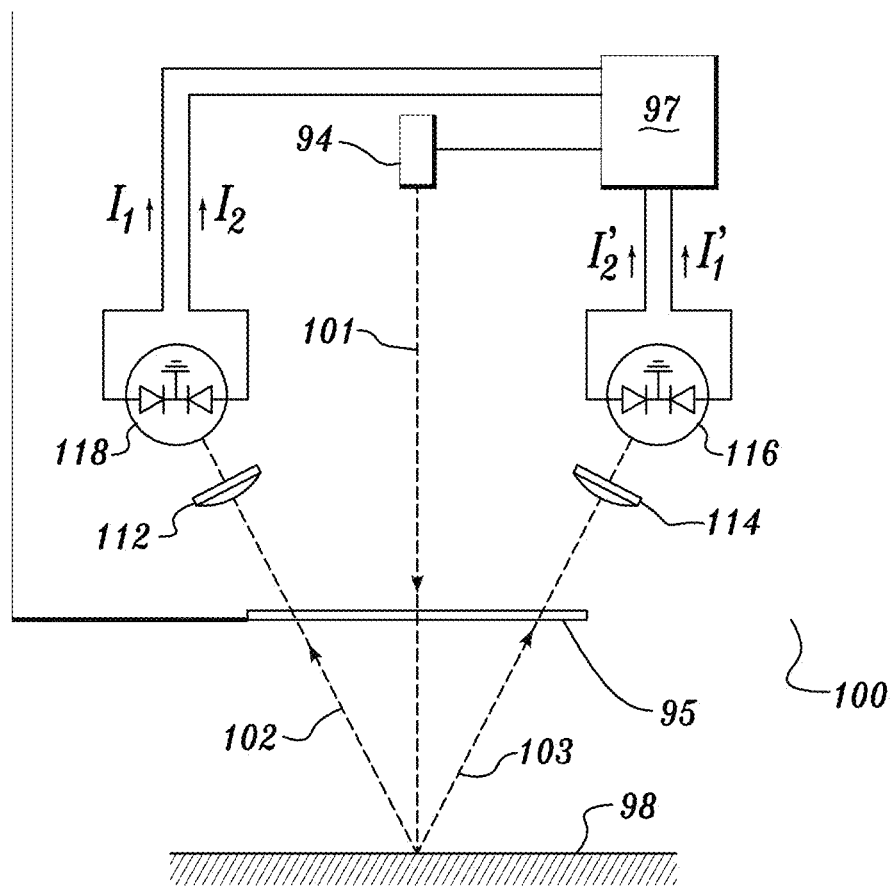
FIG. 8 is a schematic diagram of a pavement sensor showing an embodiment of the dual symmetric optical triangulation used in accordance with the invention.

The pavement height sensors of FIG. 8 operate on the principle of dual symmetric optical triangulation. The angle subtended between the emitted laser 101 and the axes of the viewing lenses is preferably approximately 30°, although angles between 10° and 60° are also useful. As explained above, imaged spots of light move across the surfaces of the photodetectors as the distance between the pavement sensor and the pavement changes. The photocurrents from detector 118, $I_1$ and $I_2$, are used to determine an uncalibrated height signal q:

$$q = \frac{l_1 - l_2}{l_1 + l_2} \quad (VIII)$$

Similarly, the photocurrents from detector 116 are used to determine another uncalibrated height signal:

$$q' = \frac{l'_1 - l'_2}{l'_1 + l'_2} \quad (VIII')$$

This eliminates the effect of surface reflectivity and laser power variations. Standard digital look-up tables and curve-fitting algorithms are used to linearize the two detector systems for height changes.

Preferably, as discussed above, the laser beam is in the form of an ellipse with a 2:1 aspect ratio with the longer dimension oriented perpendicular to the direction of rolling weight deflectometer travel. This aspect ratio, along with large dimensions of the laser beam footprint in accordance with the invention, reduces the required rolling weight deflectometer tracking accuracy.

Figure 9:
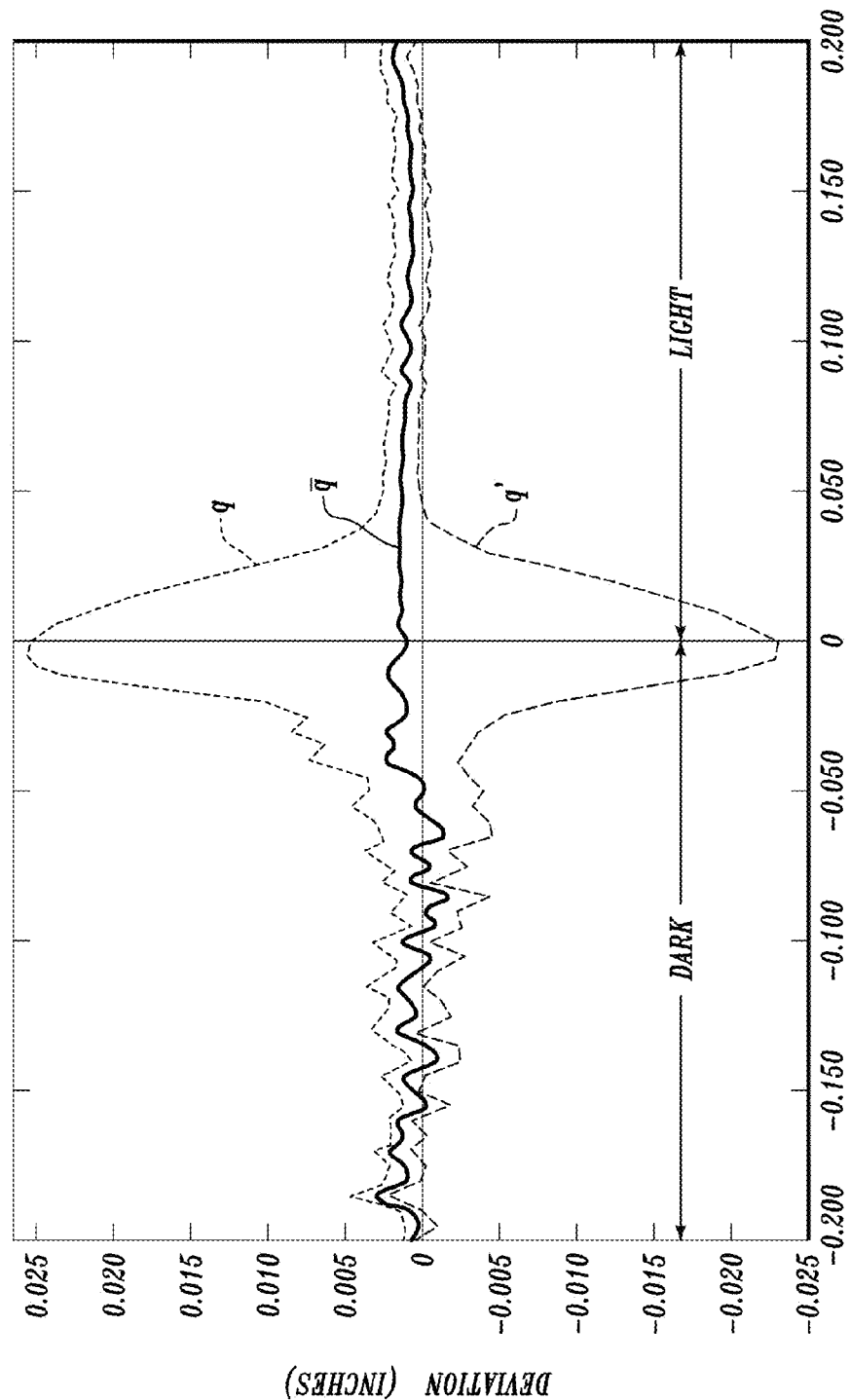
FIG. 9 is a graphical representation of contrast variation within an illuminated portion of a laser beam as imaged on two detectors using the dual symmetric optical triangulation technique.

The two detectors 118 and 116, arranged symmetrically about the laser beam, "see" the same spot on the pavement being traversed. In contrast, a triangulation sensor utilizing a single lateral effect photodiode as a position sensing detector will produce an error if the surface is not of uniform contrast. Thus, if the surface being illuminated by the laser is not of uniform contrast, then the image spot on the detector is also not of uniform contrast. The signal developed is then biased towards the brighter portion of the imaged light spot. To reduce this effect, the laser spot on the spatially sensitive photodiode is usually made very small. However, this leads to other system defects and demands, such as a need for higher sampling rates, less tolerance on rolling weight deflectometer tracking, and decreased depth of field. Adding the second symmetrical sensor, in accordance with the invention, removes height errors caused by surface contrast ambiguities and allows use of a large beam diameter. Because of symmetry, one sensor produces a larger height signal, and the other produces a smaller height signal when a high contrast edge is within the footprint of an incident laser beam. The average of the two signals produces a height signal:

$$\bar{q} = (q+q')/12 \quad (IX)$$

that is relatively insensitive to surface contrast variations within the diameter of the laser beam. This effect is graphically illustrated in FIG. 9, which shows the output from each of two detectors along with the average output, when a light/dark edge was passed through the laser beam. The output uncalibrated height signal q from photodetector 118 was plotted, along with the output uncalibrated height signal q' from photodetector 116. The calculated average q was then plotted. As can be seen, the use of this technique avoids excursions in uncalibrated height readings when the sensor passes from a dark to light area of the pavement, or vice versa. The average uncalibrated height q shows little variation with pavement reflectivity. Thus, the invention's use of dual symmetric optical triangulation provides a significant advantage over prior art measuring techniques.

Other instruments, such as a charge coupled device (CCD) could also be used as the spatial detector for the pavement sensor and the beam straightness sensor. The use of a lateral effect photodiode, while preferred, is not exclusive. Due to its many pixels, a CCD sensor can sense an intensity profile of light reflected from a pavement. However, the dual symmetric optical triangulation method would still be used to cancel contrast variations which occur within the diameter of the laser beam footprint.

Figure 10:
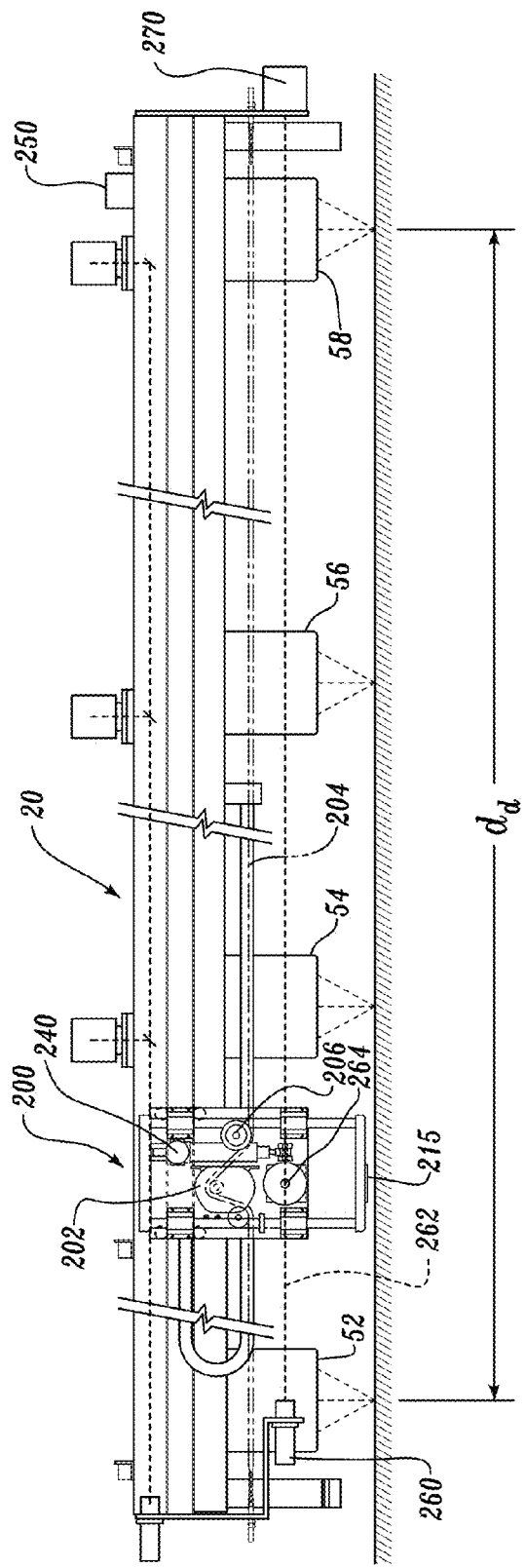
FIG. 10 is a partial schematic side view of an embodiment of a rolling weight deflectometer of the invention showing an attached calibration carriage.
Figure 10A:
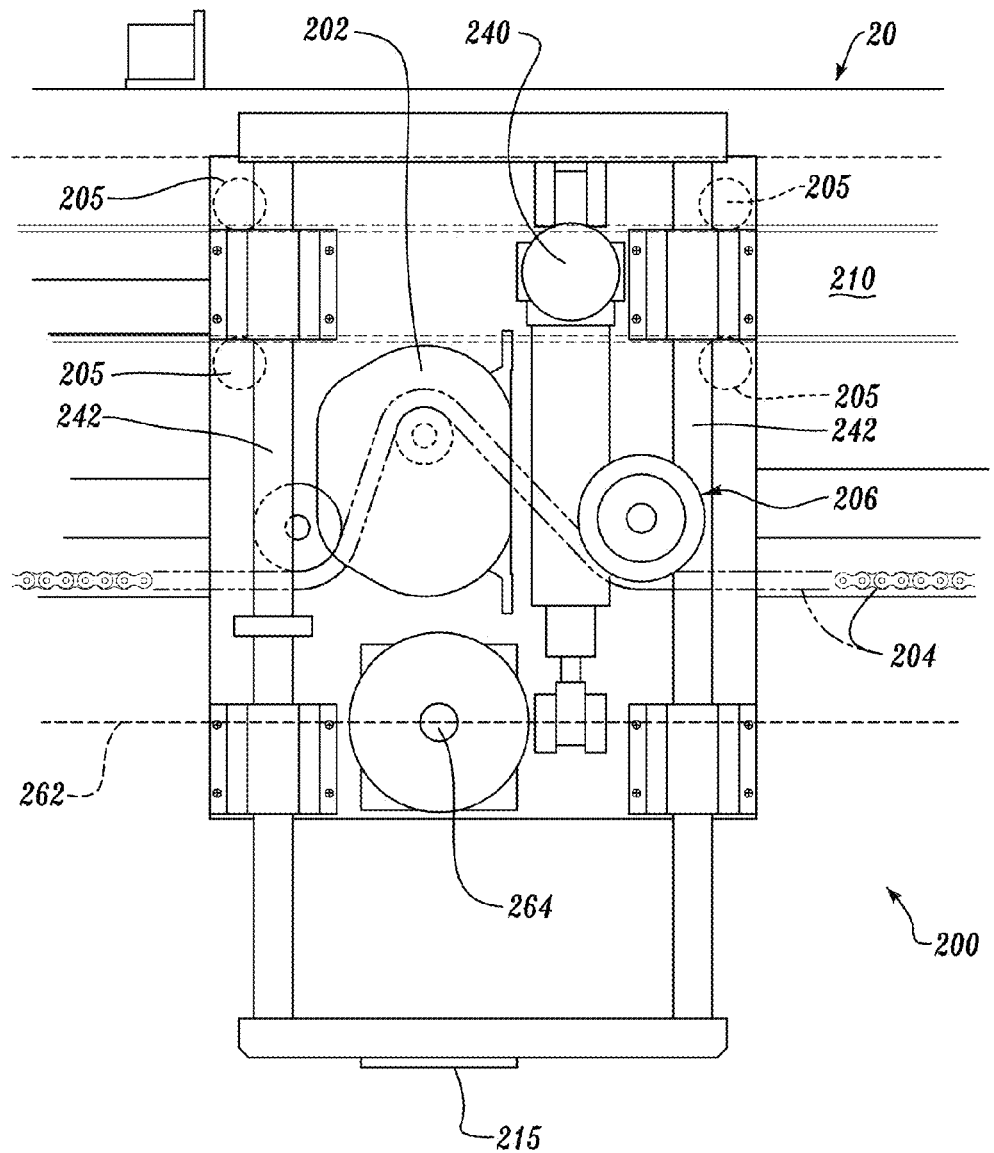
FIG. 10A is an enlarged view of the calibration carriage, showing additional detail.
Figure 10B:
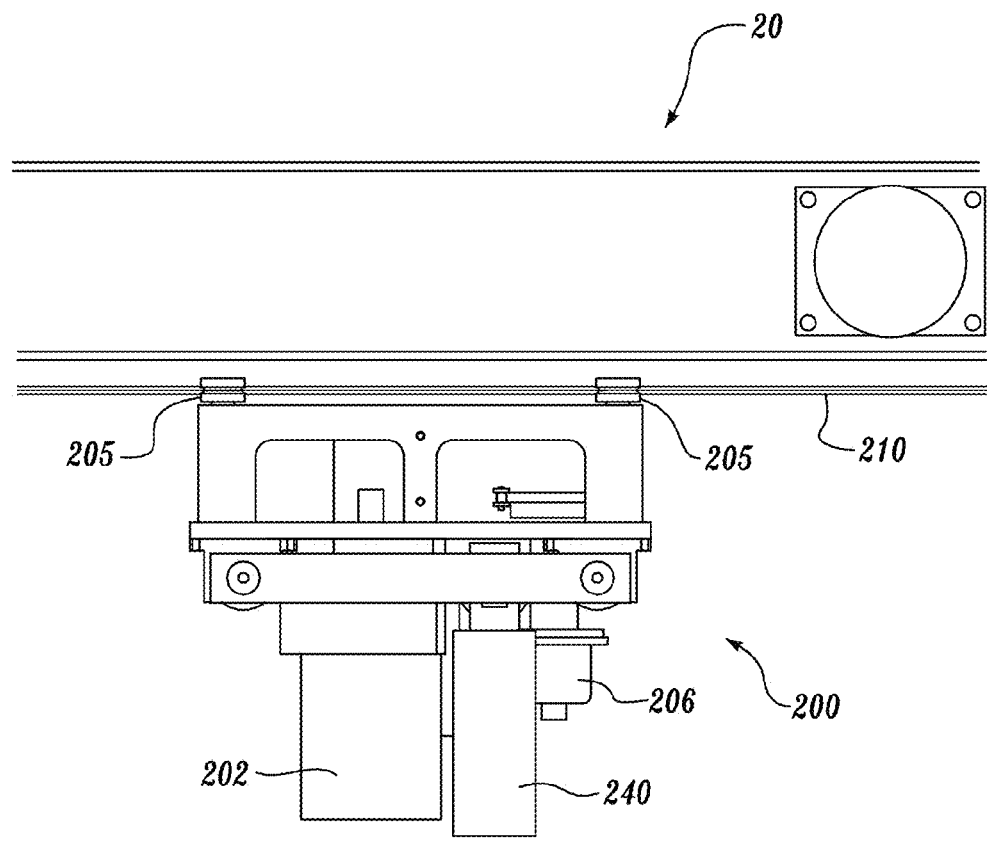
FIG. 10B is a top view of the calibration carriage, showing how it is mounted to the rolling weight deflectometer.

In another aspect of the invention, the rolling weight deflectometer is provided with a calibration system that includes a flat reference surface for pavement sensors. The establishment of such a reference surface is important for the deflection algorithm to operate successfully. It is not practicable to produce a long section of perfectly flat material, having a variation of less than 0.001 inches (25 microns) over a 15- to 30-foot member length. Thus, the invention utilizes a calibration laser beam in conjunction with a movable short section calibration plate, no larger than about the footprint of the laser beam. According to the invention, this calibration technique does not require movement of the member 20 and does not require a long flat surface. The flat calibration plate is moved successively into view of each of the pavement sensors. To achieve this, the invention provides a calibration laser emitter located at one end of the sensor-bearing member that emits a laser beam through to a beam splitter and a position sensor mounted on the calibration carriage. As the plate is moved from one pavement sensor to another, its vertical position is monitored by storing both the position of the plate, as read by its position sensor, and the height of the plate, as read by the pavement sensor, in a digital signal processor. The lightweight calibration plate, and its beam position sensor, can be temporarily attached to each successive pavement sensor. But, it is preferred, and more convenient to automatically move the plate using a motorized carriage 200 attached to the main member 20, as shown in FIGS. 10, 10A and 10B. The carriage is self-propelled by a motor 202, preferably using a sprocket and chain drive arrangement. The chain 204 rests in a long tray, parallel to the main member 20, and is threaded through the carriage motor drive mechanism while also driving a sprocket attached to a position encoder 206. Pulses from this encoder provide carriage position information, as will be explained below.

As can be seen from FIGS. 10, 10A and 10B, the carriage 200 has two sets of wheels 205 rotatably mounted near an upper end thereof. These wheels are each circumferentially grooved (see FIG. 10B) to engage opposing upper and lower edges of a carriage bearing rail 210. The carriage bearing rail is desirably of a rigid material that does not significantly flex under the weight of the carriage. Preferably, the bearing rail 210 is a flat metallic rail mounted fixedly to, and extending substantially along the entire length of, the main member 20. Thus, the carriage is able to traverse the length of the carriage bearing rail 210. Optional limiting switches may be placed at extremities of the bearing rail 210 to limit the traversal of the carriage 200.

As explained above, the purpose of the calibration carriage is to provide a means for calibrating each of the pavement distance sensors. For this purpose, the calibration carriage is equipped with a flat plate 215 of adjustable height. Preferably, the plate is a flat smooth-surfaced sheet of aluminum, more preferably painted to mimic scattering and reflectivity characteristics of pavement, such as a dull gray, and devoid of surface texture. A second motor 240, mounted on the carriage 200, drives the flat calibration plate 215 into a desired height when it is positioned beneath each of the pavement sensors. The plate motor 240 controls the concerted reciprocal movement of a pair of linear guides 242 that are fixedly attached to the plate thereby adjusting the position of the flat plate, upwardly and downwardly, until a desired plate position is obtained. Preferably, the motorized carriage may be stowed when not in use.

The invention also provides a method for compensating the pavement sensor calibration for errors introduced by the weight of the calibration carriage. In a first method, a calibration alignment laser is temporarily mounted on the ground. The calibration method explained below uses the following notation:

A, B, C and D are the distance measurements from the pavement sensors 58, 56, 54, and 52, respectively;

b, c and d are the distance values from the straightness sensors;

$I_a$ is the initial distance value from the carriage mounted straightness sensor at 58;

$I_x$ is the distance value from the carriage mounted straightness sensor taken at pavement distance sensor x where x=56, 54 or 52;

$b_o$, $c_o$ and $d_o$ are the distance readings of the member straightness sensors before calibration;

$d_b$ is the distance between the calibration alignment laser and pavement sensor 56;

$d_e$ is the distance between the calibration alignment laser and pavement sensor 54: and $d_d$ is the distance between the calibration alignment laser and pavement sensor 52 (i.e., the distance between sensor 52 and sensor 58).

These distance readings represent movement in the vertical direction only. The calibration is initiated by placing a calibration laser beam emitter on the ground and aligning the emitter so that its laser beam passes through the carriage mounted straightness sensor, regardless of the location of the carriage along the bearing member. It is important that the ground-mounted calibration laser should not move, nor be deflected in any way, during the calibration. Since the calibration laser emitter is not attached to the bearing member, its emitted laser beam is not influenced by the weight of the carriage. Moreover, atmospheric turbulence does not affect laser accuracy over short distances. Further, taking many readings and averaging these readings allows for better calibration. It is also important that the flat calibration plate of the calibration carriage should remain in a stable fixed position. This is assured by locking the plate in place, when the carriage is moved to its required position.

The use of the ground-mounted calibration laser is to ensure that all the pavement distance sensors will be "aligned in a straight line after calibration." This alignment is not by physical or mechanical adjustment, but by adjusting the output values of these pavement distance sensors, to provide the same effect as if they were physically adjusted. It is important to note that the pavement sensors need not be on the same vertical level with each other, they should, however, be collinear. This is achieved by the following procedure. Firstly, the carriage is moved to a calibration position beneath pavement sensor 58. The flat calibration plate is lowered and locked into place. Preferably, the plate should be in the middle of the operating range of the pavement sensor. Three calibration readings $b_o$, $c_o$, and $d_o$ are taken. The carriage is then moved to the next pavement sensor, sensor 56. Readings B, b and $I_b$ are taken. The carriage is then moved to the third pavement sensor 54. Readings C, c and $I_c$ are taken. Finally, the carriage is moved to the last pavement sensor 52, where readings D, d and $I_d$ are taken. Data gathering is now complete. Compensation factors for the effect of the weight of the carriage as it moves from sensor to sensor, are now computed. In order to do this, three data points are needed: a distance measurement from the pavement distance sensor, a measurement from the carriage mounted sensor, and a measurement from the reference sensor, for each of the pavement distance sensors.

1. $A_c=A$; (taken to be an end point which does not move); (X)

2. $B_c=(B+(b-b_o)+(I_b-I_a))$; (XI)

3. $C_c=(C+(c-c_o)+(I_c-I_a))$; and (XII)

4. $D_c=(D+(d-d_o)+(I_d-I_a))$. (XIII)

Clearly, if the sensor bearing member was completely rigid, and did not bend, then equations 2-4 would simplify since the differences calculated in parentheticals would equal zero.

$A_c$ and $D_c$ are taken as the end points of a desired straight line. The aim is to determine by how much $B_c$ and $C_c$ are offset from this straight line drawn between $A_c$ and $D_c$. The slope of this line is:

$$m = \frac{(A_d - D_c)}{d_d}$$ (XIV)

Using the equation for a straight line, (y=mx+k), the Y intercept, k, is set as $A_c$.
Therefore, the final compensation applied to pavement sensors B and C is:

$B_{cfinal}=B_c-((A_c-D_c)(d_b/d_d))$; (XV)

$C_{cfinal}=C_c-((A_c-D_c)(d_c/d_d))$; (XVI)

$A_{cfinal}=A_c$; and (XVII)

$D_{cfinal}=D_c$. (XVIII)

The $B_{cfinal}$ and $C_{cfinal}$ are offsets applied to the real-time data from the pavement sensors.

In a second calibration method of the invention, a carriage calibration laser is fixedly attached to an end of the main bearing member 20 and measures the position of the calibration carriage as it is guided by a track on the member. With reference to FIG. 10, a carriage calibration laser 260 is mounted at one end of the main member 20. This laser emits a beam 262 (shown in dashed lines) that travels along the length of the main member, and is incident upon an intermediate target 264 on the carriage 200. This laser beam allows the measurement of the displacement of the carriage 200 in a direction laterally away from the main member 20. Thus, as the carriage traverses the length of the member, stopping under each pavement sensor to take calibration readings, the lateral position of the calibration carriage is also measured by carriage calibration laser 260. To facilitate understanding of this method, the following descriptive notation will be used:

A, B, C and D are the distance measurements from pavement distance sensors 58, 56, 54, and 52, respectively;

b, c and d are the distance values from the straightness sensors associated with pavement distance sensors 56, 54, and 52, respectively;

$R_n$ is the distance read at the end reference straightness sensor 270 when the calibration carriage is at pavement distance sensor n;

$R_o$ is the initial distance value from the end reference straightness sensor before calibration;

$I_a$ is the initial distance value from the carriage mounted straightness sensor at sensor 58;

h is the distance value from the carriage mounted straightness sensor, where x=b, c or d, relating to sensors 56, 54 and 52, respectively;

$b_o$, $c_o$ and $d_o$ are the distance values of the member straightness sensors before calibration;

$d_b$ is the distance between the calibration alignment laser and pavement sensor 56;

$d_c$ is the distance between the calibration alignment laser and pavement sensor 54;

$d_d$ is the distance between the calibration alignment laser and pavement sensor 52; and L is the distance between the calibration alignment laser and reference target or alignment laser 270.

Calibration is initiated with the carriage at the first pavement sensor 58, where the alignment laser 260 is located. In this type of flat datum calibration, it is assumed that there are two points in space that do not move. These points are the middle of pavement sensor 52, and the reference target 270. Secondly, it is assumed that the flat calibration plate is completely immobile. This is assured by locking the plate in place. As with the ground-level laser alignment technique, the flat datum calibration technique is also based on aligning the pavement distance sensors in a straight line, not mechanically, but by adjusting output values. Also, the pavement sensors need not be level, but merely collinear with each other.

When the calibration carriage has been moved to pavement distance sensor 58, and the calibration plate is locked into place, the plate is preferably in the middle of the operating range of the pavement sensor. The following readings are taken and stored in a digital signal processor: $R_o$, $b_o$, $c_o$, $d_o$, A, and $I_a$. The carriage is then moved to pavement distance sensor 56, and the following readings are taken and stored: B, b, $I_b$, and $R_b$.

Likewise, readings are taken at pavement sensor 54 and 52.

Once data gathering and storage has been accomplished, bending compensated values Ac, Bc, Cc, and Dc are determined:

1. $Ac=A$; (taken to be an end point which does not move); (XIX)

2. $Bc=(B+(b-b_o)\pm(I_b-I_a))-(d_b/L)(R_o-R_b)$; (XX)

3. $Cc=(C+(c-c_o)\pm(I_c-I_a))-(d_c/L)(R_o-R_c)$; and (XXI)

4. $Dc=(D+(d-d_o)\pm(I_d-I_a))-(d_d/L)(R_o-R_d)$. (XXII)

If the sensor bearing member 20 were infinitely rigid, and did not bend, the various $R_n$ would not be different from $R_o$.

Thus, the equations 2, 3 and 4 would vanish. Likewise, if $B_o$, $c_o$ and $d_o$ were the same as b, c and d, respectively, then the first equations 2, 3 and 4 would simply equate to B, C and D, respectively.

Finally, the pending compensated values are "adjusted so that they are in a straight line". Again, this does not mean mechanical or physical adjustment, but adjusting outputs, by the same method described above relating to the ground-mounted laser calibration technique. Thus, the final compensation applied to pavement sensors 54 and 56 are:

$$Bc_{final} = Bc - ((Ac - Dc)(d_b/d_d)); \text{ and} \tag{XXIII}$$

$$Cc_{final} = Cc - ((Ac - Dc)(d_c/d_d)); \tag{XXIV}$$

Since the two points representing distance measurements at sensors 52 and 58 are at the ends of the straight line:

$$Ac_{final} = Ac; \text{ and} \tag{XXV}$$

$$Dc_{final} = Dc. \tag{XXVI}$$

The calibration carriage, as indicated above, includes an optical encoder 206 that records the position of the calibration carriage. This encoder sends an electrical signal to a digital signal processor 250 that keeps track of the position of the carriage. Thus, as the carriage 200 moves along the bearing rail 210, the optical encoder continuously tracks carriage movement. When the carriage is properly positioned beneath a pavement sensor, its progress is either halted automatically, by a signal from the digital signal processor that has recorded these predetermined stop positions, or by an operator, manually. The pavement sensor then measures the distance to the flat plate. This distance is used as an input to the calibration algorithms, given above.

In accordance with the invention, the shape of a pavement deflection basin may also be measured. This shape yields additional information about the stiffness of underlying layers. To measure the shape of the depression basin, pavement sensors and beam straightness sensors are added in pairs ahead of pavement sensors 52 and 54. For example, to measure the shape of a depression basin for a distance of six feet, at one foot intervals, six additional pavement sensors should be mounted ahead of sensor 52, and the same number ahead of pavement sensor 54. A beam straightness sensor is added above each additional pavement sensor. Thus, for each additional point in the deflection basin to be measured four additional pavement sensors are required: two pavement sensors and two beam straightness sensors. For example, FIG. 6 shows exemplary shape sensors 280 and 286 with associated beam straightness sensors 282 and 284, respectively.

Assume that the spacing between each pair of pavement distance sensors is nine feet and also that shape sensors are spaced at one foot intervals ahead of each of the pavement distance sensors 52 and 54. These shape sensors incorporate the dual optical triangulation technology illustrated in FIG. 8. The six pairs of equations for the virtual heights for each of the six pairs of shape sensors are then:

$$h1 = \frac{8}{9}A - \frac{17}{9}B + C \tag{XXVII}$$

$$h2 = \frac{7}{9}A - \frac{16}{9}B + C \tag{XXVIII}$$

$$h3 = \frac{2}{3}A - \frac{5}{3}B + C \tag{XXIX}$$

-continued $$h4 = \frac{5}{9}A - \frac{14}{9}B + C \tag{XXX}$$

$$h5 = \frac{4}{9}A - \frac{13}{9}B + C \tag{XXXI}$$

$$h6 = \frac{1}{3}A - \frac{4}{3}B + C \tag{XXXII}$$

$$h1' = \frac{8}{9}B - \frac{17}{9}C + D \tag{XXXIII}$$

$$h2' = \frac{7}{9}B - \frac{16}{9}C + D \tag{XXXIV}$$

$$h3' = \frac{2}{3}B - \frac{5}{3}C + D \tag{XXXV}$$

$$h4' = \frac{5}{9}B - \frac{14}{9}C + D \tag{XXXVI}$$

$$h5' = \frac{4}{9}B - \frac{13}{9}C + D \tag{XXXVII}$$

$$h6' = \frac{1}{3}B - \frac{4}{3}C + D \tag{XXXVIII}$$

Where $h_1$ refers to the measurement one foot ahead of pavement sensor 56, $h_2$ is two feet ahead, $h_n$, is n feet ahead.

While the rolling weight deflectometer of the invention may utilize a wheeled odometer to measure distance traveled, other tracking sensors, such as an optical correlator, may also be used. Such a correlator applies the principle of comparing two identical but time-shifted signals reflected from a surface. When the signals match, the amount of time between the signals is known. When the distance between the two sensors is known, the optical correlator can be used as an odometer. This is achieved by the correlator comparing the signals obtained as the deflectometer traverses the pavement. When the correlator finds a high degree of correlation between signals this indicates readings from successive sensors taken for the same sample of pavement. Since the distance between sensors is known, and the time period between the two correlated signals is known, the velocity of the deflectometer can be calculated as distance divided by time.

The use of the correlator as an odometer also assists in the detection of sideways movement or "crabbing" of the deflectometer. In this event, successive pavement distance sensors will not pass over the identical pavement, so that correlation between signals from the sensors will be significantly reduced. This reduced correlation is a warning to the operator that the deflectometer is crabbing and not traveling in such a manner as to allow successive pavement distance sensors to "see" substantially the same patch of pavement.

The rolling weight deflectometer of the invention may be optionally equipped with an infrared temperature sensor, located near a pavement sensor and oriented to read the temperature of the pavement surface. Preferably, the sensor is calibrated for pavement emissivity so that it measures the pavement temperature in real-time. Information from the infrared sensor may be transmitted and stored in a digital signal processor.

The rolling weight deflectometer of the invention may also be supplied with an optional satellite navigation receiver to provide accurate information regarding the position of the rolling weight deflectometer on the earth's surface. This information may also be stored in a digital signal processor so that pavement deflection data are effectively tagged to indicate their location on the earth's surface.

The instantaneous applied load of the rolling weight deflectometer may optionally be measured with a load cell. This will produce a more accurate indication of pavement modulus by taking into account actual instantaneous load, not the static load only. Moreover, acceleration may be instantaneously monitored by an accelerometer mounted on the load platform to measure instantaneous load, if static load is known. This instantaneous load information may also be relayed to a digital signal processor for storing and use in calculating pavement deflection.

As previously discussed, the Harr algorithm implementation requires a perfectly stiff reference beam to serve as a reference for the individual height measurements, as well as requires the three points on the surface to be measured sequentially by two different combinations of three sensors. Two sensors serve to establish a reference line such that the straight line reference (laser beam) can be used as height reference for a third location. The third location is the first undeflected location for the first measurement followed by a second measurement, during which the third location is deflected by a load wheel.

As noted above, measured deflections are small in comparison to pavement surface topology variation so that the spatially averaged height measured at one location might vary significantly if the average height is measured at a slightly offset location. Accordingly, the two sequential measurements of a given pavement location must be as close to the same position as possible.

Figure 11A:
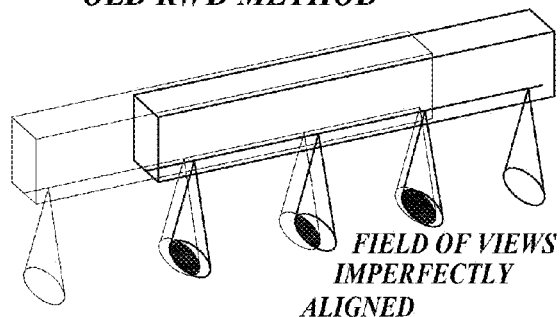
FIG. 11A is an isometric view of a currently known rolling weight deflectometer (RWD)
Figure 11B:
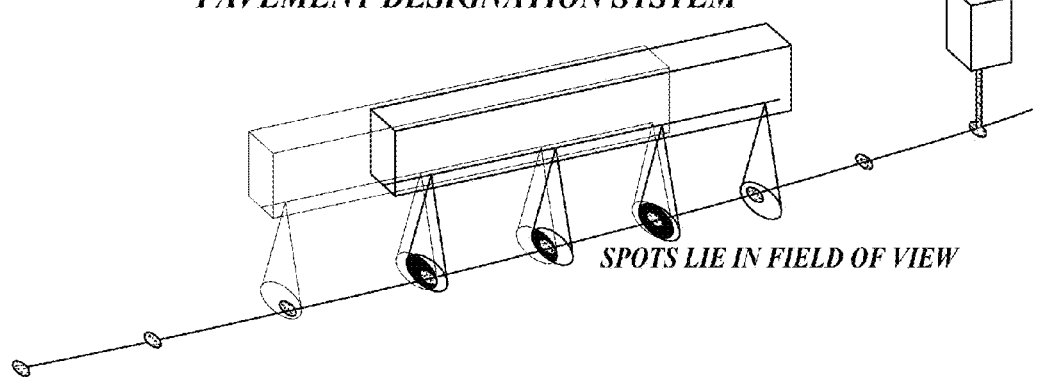
FIG. 11B is an isometric view of an embodiment of a rolling weight deflectometer with a pavement designation system.

In order to decrease inaccuracies caused by variation in the position of the measurements, several configurations, such as the one shown in FIG. 11B, are contemplated in which a measurement location on the pavement surface is "designated" by depositing a marker thereon that identifies a spot to be measured or by identifying an existing pavement feature as the spot to be measured. The marker is deposited near the leading end of the reference beam, and as the deflectometer moves forward, a marker detector located proximate to each sensor detects the marker location, and the sensor measures the height to the reference beam near the detected marker. Alternate embodiments in which the height sensor measures the marker directly are also contemplated. Further, the number and location of the marker detectors can vary to include as few as a single marker detector positioned at any location along the beam. As set forth in greater detail below, various embodiments that utilize different markers and detection systems are contemplated.

In one contemplated embodiment, the marker is a tangible medium deposited on the pavement surface. The tangible medium must be detectable by the one or more marker detectors and preferably will not leave unacceptable amounts and types of residue on the pavement surface. One material considered for use as a marker is a reflective paint. Utilizing a pulsed liquid jet or other suitable configuration mounted to the deflectometer, discreet drops of the paint are sprayed on the pavement at regular intervals. The marker detectors identify the reflection of the paint to identify the designated location, and as discussed in further detail below, the height sensor is adjusted to measure the height at the designated location. A light source is preferably directed to the markers to enhance the visibility of the markers. Further, a black swath of paint is optionally laid down before the spots of reflective paint so that the respective spots of paint are surrounded by a less reflective surface, thereby decreasing errors in marker detection.

In another contemplated embodiment, fluorescent paint or dyes are used for the markers. The fluorescent paint or dye is preferably chosen to be invisible to the naked eye, but visible when subjected to light from within a predetermined region of the ultraviolet spectrum. Ultraviolet lasers or other suitable light sources mounted proximate to the height sensors excite the paint or dye to fluoresce the markers, thereby identifying the designated surface location for measurement by the height sensors.

Figure 12:
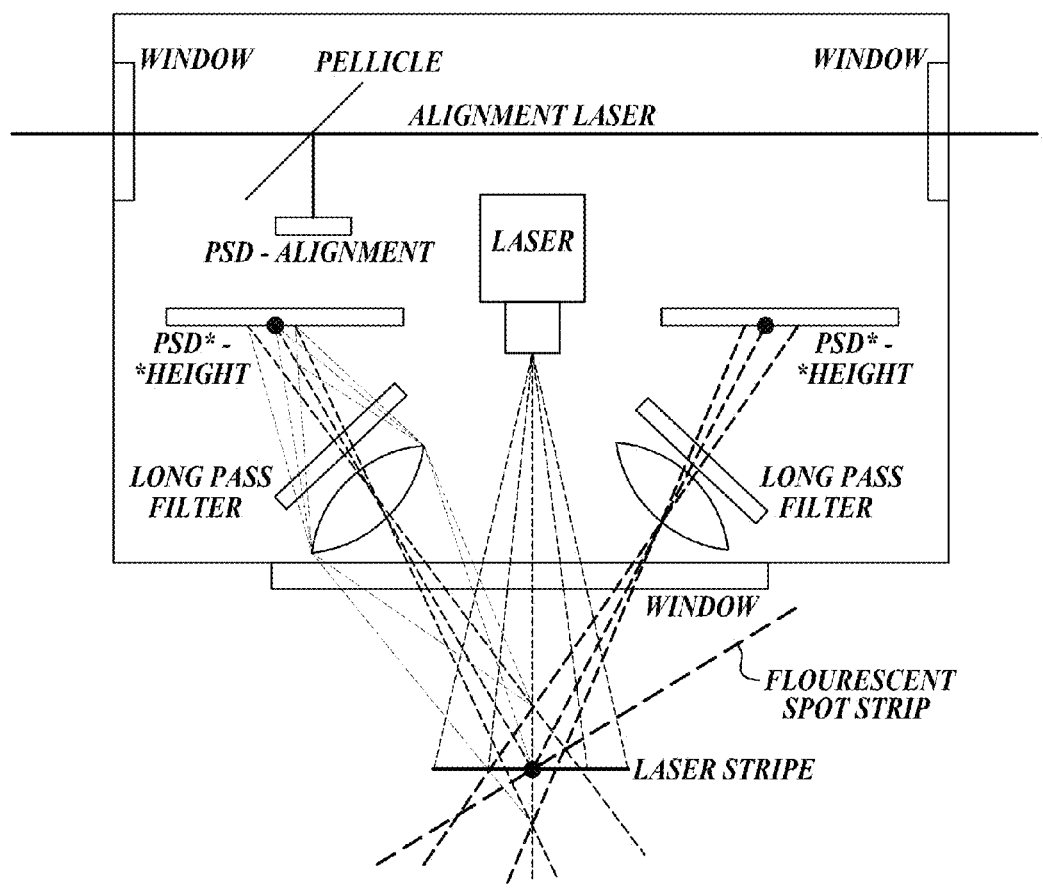
FIG. 12 is a schematic drawing of a marker detector for a pavement designation system that uses a fluorescent marker to designate measurement location.

Referring to FIG. 12, a schematic diagram of an exemplary marker detector for a fluorescent paint or dye marker is shown. The marker detector includes a laser sheet that illuminates a sufficient width of pavement to ensure that the marker is illuminated or fluoresced, even when the marker is offset from the reference beam centerline due to tracking error. The field of view of each position sensor (position sensitive detector or PSD, or a pixilated sensor such as a CMOS or CCD array) is wide enough that the marker falls within the field of view and the height of the reference beam relative to the marker can be measured. It should be appreciated that the disclosed marker detector is not limited to a particular type of sensor, and that any suitable sensor for detecting the position of a particular marker can be utilized.

While the illustrated embodiment utilizes height sensors with a wide field of view, alternate configurations for enabling the sensors to measure a height at an offset marker are contemplated. In one alternate embodiment, the reference beam and sensors are moved laterally as a unit to align the height sensors with the marker. Alternately, individual height sensors can be translated laterally or rotated to align with the marker. It is also contemplated that suitable combinations of some or all of (1) sensors with a wide field of view; (2) movement of the reference beam; and (3) translation or rotation of individual sensors are utilized. These and other suitable configurations for aligning the height sensors to the markers are contemplated and should be considered within the scope of the present disclosure.

Exemplary marker materials are disclosed above; however it should be appreciated that these examples should not be considered limiting and that other suitable materials can be used to mark the surface locations designated to be measured. Accordingly, the use of alternate materials is contemplated and should be considered within the scope of the present disclosure.

In yet another contemplated embodiment, the marker is a not a tangible material deposited on the pavement surface, but instead comprises a thermal "hot spot" on the pavement created by directing a radiative energy at the pavement. In one non-limiting example, a pulsed laser is directed at the pavement surface, creating thermal markers, i.e., warm spots on the pavement, that are readable by infrared sensors or other suitable temperature readers.

The previously discussed markers are described as being deposited on the pavement surface in discreet locations, i.e., spots in order to provide lateral and axial information about the measurement locations. In one alternate embodiment a series of discreet markers is not utilized. Instead, a marker that comprises a continuous stripe is deposited on the pavement to provide lateral position information for the measurement locations. In this embodiment, the marker is not relied upon to provide information regarding the axial position of the measurement locations. In another alternate embodiment, the marker is a generally continuous stripe with intermittent interruptions in the marker material that provides data regarding the lateral and axial position of the measurement locations. Such interruptions can be periodic or aperiodic. These and other possible embodiments utilizing different marker patterns are contemplated and should be considered within the scope of the present disclosure.

Figure 13:
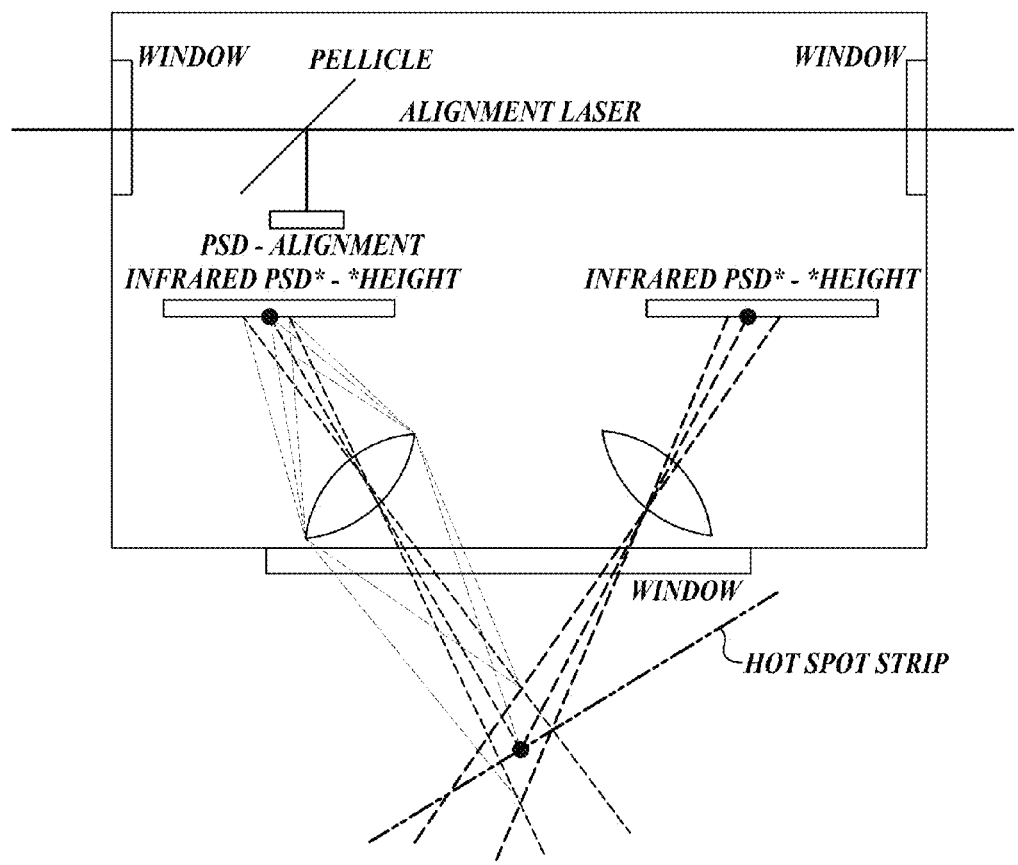
FIG. 13 is a schematic drawing of a marker detector for a pavement designation system that uses a thermal marker to designate measurement location.

Referring to FIG. 13, a schematic diagram of an exemplary marker detector for a thermal marker is shown. An array of infrared detectors, detect the marker and measure the height of the marker to the reference beam. Alternately infrared detectors can be used in tandem with optical height sensors. Such a configuration is shown in FIGS. 14A-14C, wherein a Lead Selenide (PbSe) infrared tracking system locates a marker, and an optical triangulation height sensor (OTH) measures the height at the marker, or at a fixed offset distance from the marker. It should be appreciated that the number and type of detectors can vary along with the manner in which the sensors are adjusted to account for the position of the marker. Such variations to the disclosed embodiments are contemplated and should be considered within the scope of the present disclosure.

In contrast to the previously described configurations, other embodiments that do not require depositing a marker on the pavement are contemplated for ensuring that the two sequential measurements are taken at the same pavement location. These embodiments instead identify and utilize features of the pavement to designate measurement locations. In one such alternate configuration, a lateral profile of the pavement surface is scanned at the leading edge of the reference beam and at each height sensor. These profiles are cross-correlated to identify a common surface location, and the measured heights at this common location are used to calculate the pavement deflection. More specifically, a first sensor, located at the leading edge of the reference beam scans the pavement surface to generate a lateral reference profile. As each height sensor passes over the measurement location, another lateral surface profile scan is performed. The surface profiles taken at each of the height sensors are cross-correlated with the reference profile to determine a common surface feature from each profile at which the height measurement is taken. This 2-D cross-correlation ensures that the measurements are taken at a common surface location for all height sensors. In alternate embodiment, the system is simplified by using the lateral profile scanned at the first height sensor as the reference profile for cross-correlation at the subsequent height sensors.

The above-described use of a 2-D lateral surface profile enables height measurements to be made at a repeatable location in a lateral direction. A similar technique can be applied to minimize variation in the axial direction. In this regard, a series of lateral profile scans taken in rapid succession, can generate a 3-D surface profile that enables cross-correlation in both the lateral and axial directions. Alternately, a 3-D surface profile scanner, i.e., a scanner with a 2-D array of sensors, can be used to generate a 3-D profile.

Figure 15:
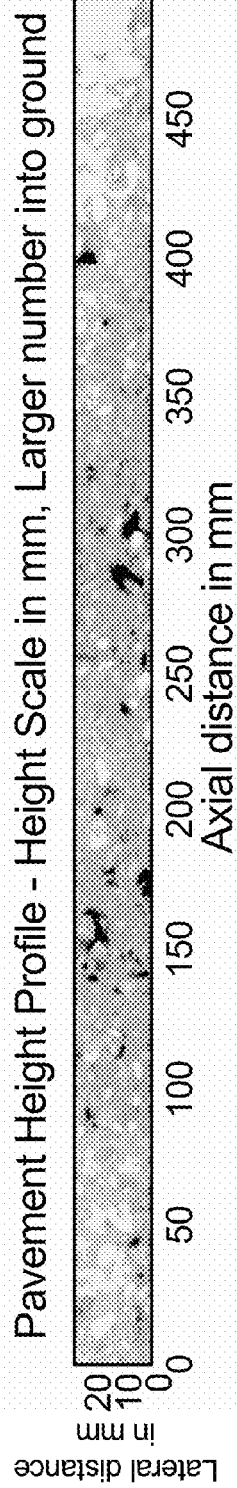
FIG. 15 is a first exemplary pair of pavement scans from a system that establishes common measurement locations by cross-correlation.
Figure 15:
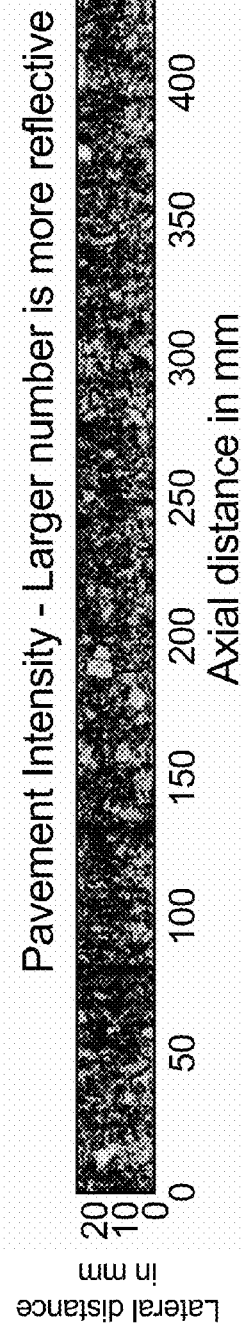
Figure 16:
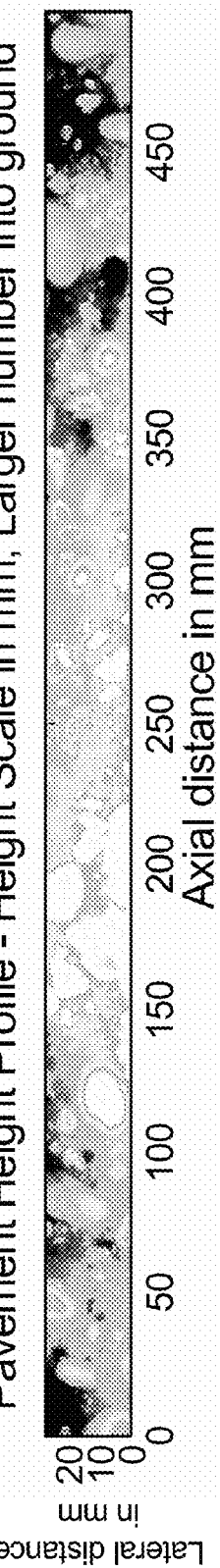
FIG. 16 is a second exemplary pair of pavement scans from a system that establishes common measurement locations by cross-correlation.
Figure 16:
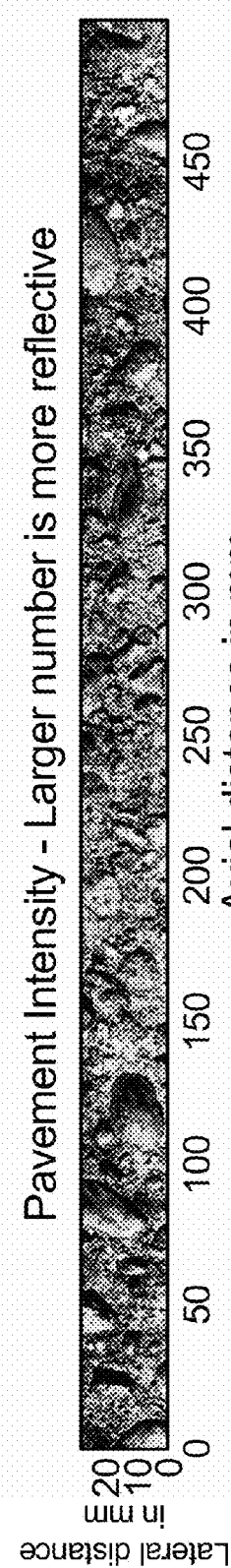

Referring to FIGS. 15 and 16, exemplary 3-D surface profiles are illustrated. The first scan of each figure shows an exemplary height profile scanned from a pavement sample. The second scan of each figure shows an exemplary intensity profile that shows the reflectivity of a pavement sample. The illustrated scans show sufficient surface topography to allow cross-correlation in both lateral and axial directions to establish measurement locations. It is contemplated that other suitable types of scans of surface features (such as reflectivity) are possible to allow for cross-cross correlation and the use of such alternate scans should be considered within the scope of the present disclosure.

With a common measurement location established by cross-correlation, the system ensures that height sensors measure the height at the correct location in a manner similar to that previously described with respect to the location designation system. In this regard, one contemplated embodiment moves the reference beam and sensors laterally as a unit to align the height sensors with the measurement location. The reference beam and sensors can also be rotated in addition to or in lieu of translation by variably positioning one or both of the leading and trailing ends of the beam. Alternately, individual height sensors can be translated laterally or rotated to align with the marker. Other contemplated embodiments utilize one or more of the following to ensure that the sensors measure the height at the proper surface location: (1) sensors with a wide field of view; (2) movement of the reference beam; and (3) adjustment of individual sensors can be utilized.

The described embodiment of the disclosed deflectometer utilizes four height sensors to measure the deflection of the pavement under the load wheel 22. This configuration, however, only measures the deflection at a single location, i.e., at the base of the load wheel 22. It is contemplated that additional sensors can be used to measure additional deflections proximate to the load wheel 22 in order to provide more detailed information of how the pavement behaves under and near the application of a load, thereby providing more detail as to the strength of the pavement. In this regard, the use of additional sensors is possible and should be considered within the scope of the present disclosure.

While illustrative embodiments have been illustrated and described, it will be appreciated that various changes can be made therein without departing from the spirit and scope of the invention.

The embodiments of the invention in which an exclusive property or privilege is claimed are defined as follows:

1. A device for measuring the deflection of pavement under an applied load, the device comprising:
   (a) a longitudinally extending member mounted on a mobile carriage;
   (b) a load platform mounted on the carriage in the vicinity of a first end of the longitudinally extending member;
   (c) a target designator depositing a marker on the pavement to designate a target location, wherein the marker is spaced at least one of axially and laterally from the target location;
   (d) a target detector detecting a position of the marker to determine the target location;
   (e) a load wheel rotatably mounted on an axle, said axle mounted near the first end of the longitudinally extending member, below the load platform, and in load bearing communication with said platform;
   (f) a first pavement sensor mounted on the longitudinally extending member, near the load wheel to measure the depth of a deflection basin created by the wheel at the target location; and
   (g) a second pavement sensor mounted on the longitudinally extending member at a predetermined distance from the first sensor to measure distance to the target location when the second pavement sensor is positioned proximate to the target location, the predetermined distance sufficiently large so that distance measurements of the second pavement sensor are substantially unaffected by a deflection basin of the load wheel.

2. The device of claim 1, further comprising a compensator, aligning the first and second pavement sensors with the target location.

3. The device of claim 2, wherein the compensator translates at least one of the first and second pavement sensors in a lateral direction.

4. The device of claim 2, wherein the compensator rotates at least one of the first and second pavement sensors.

5. A device for measuring the deflection of pavement under an applied load, the device comprising:
   (a) a longitudinally extending member mounted on a mobile carriage;
   (b) a load platform mounted on the carriage in the vicinity of a first end of the longitudinally extending member;
   (c) a target designator designating a target location disposed on the pavement, wherein the target designator deposits a marker on the pavement such that the marker is spaced at least one of axially and laterally from the target location, wherein the marker comprises a reflective paint;
   (d) a target detector detecting the marker, the target detector comprising a light sensor for sensing the reflective paint;
   (e) a load wheel rotatably mounted on an axle, said axle mounted near the first end of the longitudinally extending member, below the load platform, and in load bearing communication with said platform;
   (f) a first pavement sensor mounted on the longitudinally extending member, near the load wheel to measure the depth of a deflection basin created by the wheel at the target location; and
   (g) a second pavement sensor mounted on the longitudinally extending member at a predetermined distance from the first sensor to measure distance to the target location when the second pavement sensor is positioned proximate to the target location, the predetermined distance sufficiently large so that distance measurements of the second pavement sensor are substantially unaffected by a deflection basin of the load wheel.

6. A device for measuring the deflection of pavement under an applied load, the device comprising:
   (a) a longitudinally extending member mounted on a mobile carriage;
   (b) a load platform mounted on the carriage in the vicinity of a first end of the longitudinally extending member;
   (c) a target designator designating a portion of the pavement as a target location, wherein the target designator deposits a marker on the pavement such that the marker is spaced at least one of axially and laterally from the target location, wherein the marker comprises a fluorescent material;
   (d) a target detector detecting the marker;
   (e) a load wheel rotatably mounted on an axle, said axle mounted near the first end of the longitudinally extending member, below the load platform, and in load bearing communication with said platform;
   (f) a first pavement sensor mounted on the longitudinally extending member, near the load wheel to measure the depth of a deflection basin created by the wheel at the target location; and
   (g) a second pavement sensor mounted on the longitudinally extending member at a predetermined distance from the first sensor to measure distance to the target location when the second pavement sensor is positioned proximate to the target location, the predetermined distance sufficiently large so that distance measurements of the second pavement sensor are substantially unaffected by a deflection basin of the load wheel.

7. The device of claim 6, wherein the target detector comprises an ultraviolet light source to fluoresce the marker.

8. A device for measuring the deflection of pavement under an applied load, the device comprising:
   (a) a longitudinally extending member mounted on a mobile carriage;
   (b) a load platform mounted on the carriage in the vicinity of a first end of the longitudinally extending member;
   (c) a target designator heating a portion of the pavement to designate a target location;
   (d) a target detector comprising a thermal sensor detecting the heated portion of the pavement;
   (e) a load wheel rotatably mounted on an axle, said axle mounted near the first end of the longitudinally extending member, below the load platform, and in load bearing communication with said platform;
   (f) a first pavement sensor mounted on the longitudinally extending member, near the load wheel to measure the depth of a deflection basin created by the wheel at the target location; and
   (g) a second pavement sensor mounted on the longitudinally extending member at a predetermined distance from the first sensor to measure distance to the target location when the second pavement sensor is positioned proximate to the target location, the predetermined distance sufficiently large so that distance measurements of the second pavement sensor are substantially unaffected by a deflection basin of the load wheel.

9. A device for measuring the deflection of pavement under an applied load, the device comprising:
   (a) a longitudinally extending member mounted on a mobile carriage;
   (b) a load platform mounted on the carriage in the vicinity of a first end of the longitudinally extending member;
   (c) a load wheel rotatably mounted on an axle, said axle mounted near the first end of the longitudinally extending member, below the load platform, and in load bearing communication with said platform;
   (d) a surface profiler, the surface profiler scanning the pavement to generate a first profile of a pavement surface, the first profile comprising a plurality of pavement surface features, the surface profiler designating one of the plurality of pavement surface features as a target location;
   (e) a first pavement sensor mounted on the longitudinally extending member, near the load wheel to measure the depth of a deflection basin created by the wheel at the target location; and
   (f) a second pavement sensor mounted on the longitudinally extending member at a predetermined distance from the first pavement sensor to measure distance to the target location when the second pavement sensor is positioned proximate to the target location, the predetermined distance being sufficiently large so that distance measurements of the second pavement sensor are substantially unaffected by a deflection basin of the load wheel.

10. The device of claim 9, wherein the surface profiler scans the pavement proximate to the second pavement sensor to generate a second profile of the pavement surface, the surface profiler correlating the second profile to the first profile to identify the target location on the second profile.

11. The device of claim 10, wherein the first profile is a two dimensional profile.

12. The device of claim 11, wherein the first profile extends in a lateral direction.

13. The device of claim 10, wherein the first profile is a three dimensional profile.

* * * * *

UNITED STATES PATENT AND TRADEMARK OFFICE
CERTIFICATE OF CORRECTION

PATENT NO. : 9,448,148 B2  
APPLICATION NO. : 13/871951  
DATED : September 20, 2016  
INVENTOR(S) : R. W. McCullough et al.

Page 1 of 1

It is certified that error appears in the above-identified patent and that said Letters Patent is hereby corrected as shown below:

| Column | Line | Error |
|---|---|---|
| Item (74) Pg. 1, Column 2 | Attorney, Agent, or Firm | "Chrsitensen O'Connor Johnson Kindness PLLC" should read --Christensen O'Connor Johnson Kindness PLLC-- |

Signed and Sealed this  
Seventh Day of March, 2017

Michelle K. Lee  
*Director of the United States Patent and Trademark Office*